(12) United States Patent
Djupesland et al.

(10) Patent No.: US 10,398,859 B2
(45) Date of Patent: Sep. 3, 2019

(54) NASAL DELIVERY DEVICES

(71) Applicant: OptiNose AS, Oslo (NO)

(72) Inventors: Per Gisle Djupesland, Oslo (NO); Roderick Peter Hafner, Wiltshire (GB); Colin David Sheldrake, Wiltshire (GB)

(73) Assignee: OptiNose AS, Oslo (NO)

( * ) Notice: Subject to any disclaimer, the term of this patent is extended or adjusted under 35 U.S.C. 154(b) by 825 days.

(21) Appl. No.: 14/798,221

(22) Filed: Jul. 13, 2015

(65) Prior Publication Data

US 2016/0095989 A1 Apr. 7, 2016

Related U.S. Application Data

(63) Continuation of application No. 14/058,647, filed on Oct. 21, 2013, now Pat. No. 9,108,015, which is a (Continued)

(30) Foreign Application Priority Data

Sep. 15, 2004 (GB) .................................. 0420513.4

(51) Int. Cl.
*A61M 16/00* (2006.01)
*A61M 15/00* (2006.01)
(Continued)

(52) U.S. Cl.
CPC ...... *A61M 15/002* (2014.02); *A61M 15/0021* (2014.02); *A61M 15/0028* (2013.01);
(Continued)

(58) Field of Classification Search
CPC ........ A61M 2202/064; A61M 15/0021; A61M 15/08; A61M 15/0086; A61M 15/0098;
(Continued)

(56) References Cited

U.S. PATENT DOCUMENTS 605,436 A 6/1898 Kellogg
642,748 A 2/1900 Manners
(Continued)

FOREIGN PATENT DOCUMENTS

CN A-1342093 3/2002
EP 0820780 1/1998
(Continued)

OTHER PUBLICATIONS

Cindy H. Dubin, *Nothing to Sneeze At*, Pharmaceutical Formulation & Quality Magazine (Jan. 29, 2003).
(Continued)

*Primary Examiner* — Steven O Douglas
(74) *Attorney, Agent, or Firm* — Finnegan, Henderson, Farabow, Garrett & Dunner, LLP

(57) ABSTRACT

A nasal delivery device for and method of delivering substance to a nasal cavity of a subject, the delivery device comprising: a container-receiving unit comprising a container chamber for receiving a substance-containing container which contains substance to be delivered to the nasal cavity of the subject, the container chamber including an inlet and an outlet; a nosepiece unit including a nosepiece for fitting to a nasal cavity of the subject and being in fluid communication with the outlet of the container chamber; a mouthpiece unit including a mouthpiece in fluid communication with the inlet of the container chamber and through which the subject in use exhales, such as to entrain substance from the container and deliver the same through the nosepiece; and moisture-mitigation means for mitigating an effect of moisture in an exhaled breath on the entrainment of substance from the container, which means are provided, for example, by providing the container in a replaceable container-containing member, by a pressure-sensitive valve which normally closes the fluid connection between the
(Continued)

container chamber and the mouthpiece, and a temperature regulator upstream of the container chamber.

4 Claims, 18 Drawing Sheets

Related U.S. Application Data continuation of application No. 13/471,146, filed on May 14, 2012, now Pat. No. 8,590,530, which is a continuation of application No. 11/663,099, filed as application No. PCT/GB2005/003549 on Sep. 15, 2005, now abandoned.

(51) Int. Cl.
*A61M 15/08* (2006.01)
*A61M 16/10* (2006.01)

(52) U.S. Cl.
CPC .... *A61M 15/0035* (2014.02); *A61M 15/0041* (2014.02); *A61M 15/0045* (2013.01); *A61M 15/0086* (2013.01); *A61M 15/0091* (2013.01); *A61M 15/0098* (2014.02); *A61M 15/08* (2013.01); *A61M 16/1055* (2013.01); *A61M 16/1065* (2014.02); *A61M 16/1075* (2013.01); *A61M 2202/064* (2013.01)

(58) Field of Classification Search
CPC ............ A61M 15/002; A61M 15/0035; A61M 15/0041; A61M 15/0028; A61M 15/0045; A61M 15/0091; A61M 16/1065; A61M 16/1055; A61M 16/1075
See application file for complete search history.

(56) References Cited

U.S. PATENT DOCUMENTS

| | | |
|---|---|---|
| 658,436 A | 9/1900 | Groth |
| 746,749 A | 12/1903 | Seidel |
| 794,641 A | 7/1905 | Ramey |
| 902,832 A | 11/1908 | Philbrook |
| 3,888,252 A | 6/1975 | Side et al. |
| 3,906,950 A * | 9/1975 | Cocozza ............ A61M 15/0028 128/203.15 |
| 3,971,377 A | 7/1976 | Damani |
| 4,796,614 A | 1/1989 | Nowacki |
| 5,038,769 A | 8/1991 | Krauser |
| 5,201,308 A | 4/1993 | Newhouse |
| 5,666,948 A | 9/1997 | Matson |
| 5,685,294 A * | 11/1997 | Gupte ................ A61M 15/0028 128/203.15 |
| 5,715,811 A | 2/1998 | Ohki et al. |
| 5,797,390 A | 8/1998 | McSoley |
| 5,797,392 A | 8/1998 | Keldmann et al. |
| 5,899,202 A | 5/1999 | Ohki et al. |
| 5,964,417 A | 10/1999 | Aman et al. |
| 6,186,141 B1 | 2/2001 | Pike et al. |
| 6,257,233 B1 | 7/2001 | Burr et al. |
| 6,546,929 B2 | 4/2003 | Burr et al. |
| 6,648,848 B1 | 11/2003 | Keldmann et al. |
| 6,715,485 B1 | 4/2004 | Djupesland |
| 6,901,929 B2 | 6/2005 | Burr et al. |
| D530,815 S | 10/2006 | Murphy et al. |
| 7,252,087 B2 | 8/2007 | Wachtel |
| 7,347,201 B2 | 3/2008 | Djupesland |
| 7,377,901 B2 | 5/2008 | Djupesland et al. |
| 7,422,013 B2 | 9/2008 | Burr et al. |
| 7,481,218 B2 | 1/2009 | Djupesland |
| 7,543,581 B2 | 6/2009 | Djupesland |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 7,934,503 B2 | 5/2011 | Djupesland et al. |
| 7,975,690 B2 | 7/2011 | Djupesland |
| 8,047,202 B2 | 11/2011 | Djupesland |
| 8,146,589 B2 | 4/2012 | Djupesland |
| 8,161,969 B2 | 4/2012 | Burr et al. |
| 8,171,929 B2 | 5/2012 | Djupesland et al. |
| 8,327,844 B2 | 12/2012 | Djupesland |
| 8,511,303 B2 | 8/2013 | Djupesland |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,590,530 B2 | 11/2013 | Djupesland et al. |
| 8,596,278 B2 | 12/2013 | Djupesland |
| 8,800,555 B2 | 8/2014 | Djupesland |
| 8,875,704 B2 | 11/2014 | Djupesland et al. |
| 8,899,229 B2 | 12/2014 | Djupesland et al. |
| 8,910,629 B2 | 12/2014 | Djupesland et al. |
| D723,156 S | 2/2015 | Djupesland et al. |
| D725,769 S | 3/2015 | Djupesland et al. |
| 8,978,647 B2 | 3/2015 | Djupesland et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| D759,805 S | 6/2016 | Djupesland |
| D761,951 S | 7/2016 | Djupesland |
| 9,452,272 B2 | 9/2016 | Djupesland et al. |
| 9,468,727 B2 | 10/2016 | Djupesland |
| D773,644 S | 12/2016 | Djupesland |
| 9,522,243 B2 | 12/2016 | Djupesland |
| 9,566,402 B2 | 2/2017 | Djupesland |
| 9,649,456 B2 | 5/2017 | Djupesland et al. |
| 2002/0017297 A1 | 2/2002 | Burr et al. |
| 2003/0209243 A1 | 11/2003 | Burr et al. |
| 2004/0024330 A1 | 2/2004 | Djupesland et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0149289 A1 | 8/2004 | Djupesland |
| 2004/0173211 A1 | 9/2004 | Kladders et al. |
| 2004/0182388 A1 | 9/2004 | Djupesland |
| 2005/0028812 A1 | 2/2005 | Djupesland |
| 2005/0072430 A1 | 4/2005 | Djupesland |
| 2005/0235992 A1 | 10/2005 | Djupesland |
| 2006/0048780 A1 | 3/2006 | Burr et al. |
| 2006/0096589 A1 | 5/2006 | Djupesland |
| 2006/0107957 A1 | 5/2006 | Djupesland |
| 2006/0169278 A1 | 8/2006 | Djupesland et al. |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2006/0254583 A1 | 11/2006 | Deboeck et al. |
| 2007/0039614 A1 | 2/2007 | Djupesland |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland et al. |
| 2008/0223363 A1 | 9/2008 | Djupesland |
| 2008/0230058 A1 | 9/2008 | Burr et al. |
| 2008/0289629 A1 | 11/2008 | Djupesland et al. |
| 2009/0101146 A1 | 4/2009 | Djupesland |
| 2009/0293873 A1 | 12/2009 | Djupesland et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |

(56) References Cited

U.S. PATENT DOCUMENTS

| | | |
|---|---|---|
| 2010/0057047 A1 | 3/2010 | Djupesland et al. |
| 2010/0242959 A1 | 9/2010 | Djupesland et al. |
| 2010/0282246 A1 | 11/2010 | Djupesland et al. |
| 2010/0288275 A1 | 11/2010 | Djupesland et al. |
| 2010/0300439 A1 | 12/2010 | Djupesland et al. |
| 2010/0300440 A1 | 12/2010 | Deboeck et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0095993 A1 | 4/2016 | Djupesland |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |
| 2016/0331916 A1 | 11/2016 | Djupesland et al. |
| 2016/0367771 A1 | 12/2016 | Djupesland |
| 2016/0367772 A1 | 12/2016 | Djupesland |
| 2016/0367774 A1 | 12/2016 | Djupesland et al. |
| 2017/0043108 A1 | 2/2017 | Djupesland et al. |
| 2017/0151397 A1 | 6/2017 | Djupesland |
| 2017/0203061 A1 | 7/2017 | Djupesland et al. |
| 2017/0216540 A1 | 8/2017 | Djupesland |

FOREIGN PATENT DOCUMENTS

| | | |
|---|---|---|
| EP | 1177807 | 2/2002 |
| EP | 1407795 | 4/2004 |
| GB | 1396258 | 6/1975 |
| GB | 2405350 | 3/2005 |
| GB | 2404867 | 2/2006 |
| JP | 5-277189 A | 10/1993 |
| JP | 08-506504 | 7/1996 |
| JP | 08-0238318 | 9/1996 |
| JP | 8-322933 A | 12/1996 |
| JP | A-09/140791 | 6/1997 |
| JP | A-10/155907 | 6/1998 |
| JP | 10-234827 | 9/1998 |
| JP | 2001-95918 A | 4/2001 |
| JP | A-2001-526577 | 12/2001 |
| JP | A-2002-537908 | 11/2002 |
| JP | A-2005/521485 | 7/2005 |
| RU | C-2258538 | 3/2000 |
| WO | WO-92/03175 | 3/1992 |
| WO | WO 96/22802 | 8/1996 |
| WO | WO 1998/034664 | 8/1998 |
| WO | WO 98/53869 | 12/1998 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 2003/041776 | 5/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

P.G. Djupesland, *Bi-Directional Nasal Delivery of Aerosols Can Prevent Lung Deposition*, Journal of Aerosol Medicine (Sep. 2004).

*Bi-Directional Nasal Device Delivers Drug on Exhalation*, Pharmaceutical Technology (Sep. 10, 2004).

Ola Dale et al., *Intranasal Midazolam: A Comparison of Two Delivery Devices in Human Volunteers*, Journal of Pharmacy and Pharmacology (Oct. 2004).

G. Furness, *Nasal Drug Delivery: Rapid Onset Via a Convenient Route*, ONdrugDelivery Ltd. (2005).

M. Kleven, *Using Computational Fluid Dynamics (CFD) to Improve the Bi-Directional Nasal Drug Delivery Concept*, Trans IChemE Part C. (Jun. 2005).

(56) References Cited

OTHER PUBLICATIONS

Per Gisle Djupesland, *Breath-Actuated Bi-Directional Delivery Sets the Nasal Market on a New Course*, ONdrugDelivery (Oct. 10, 2005).

Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).

P.G. Djupesland et al., *Breath Actuated Nasal Device Improves Delivery to Target Sites Beyond the Nasal Valve*, The Laryngoscope (Mar. 2006).

R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).

A. Skretting et al., *A New Method for Scintigraphic Quantification of Deposition and Clearance in Anatomical Regions of the Human Nose*, Nuclear Medicine Communications (Aug. 2009).

Vlckovia et al., *Effective Treatment of Mild-to-Moderate Nasal Polyposis with Fluticasone Delivered by a Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., Intranasal Sumatriptan Powder Delivered by a Novel Breath Actuated Bi-Directional Device for the Acute Treatment of Migraine: A Randomised Placebo-Controlled Study, Cephalalgia (Mar. 17, 2010).

F.S. Hansen et al., *Preliminary Efficacy of Fluticasone Delivered by a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).

S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study ): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

Machine translation, JP-A-09/140791.
English-Language Translation of JP5-277189(A).
English-Language Translation of JP8-322933(A).
English-Language Abstract of JP2001-95918(A).

\* cited by examiner

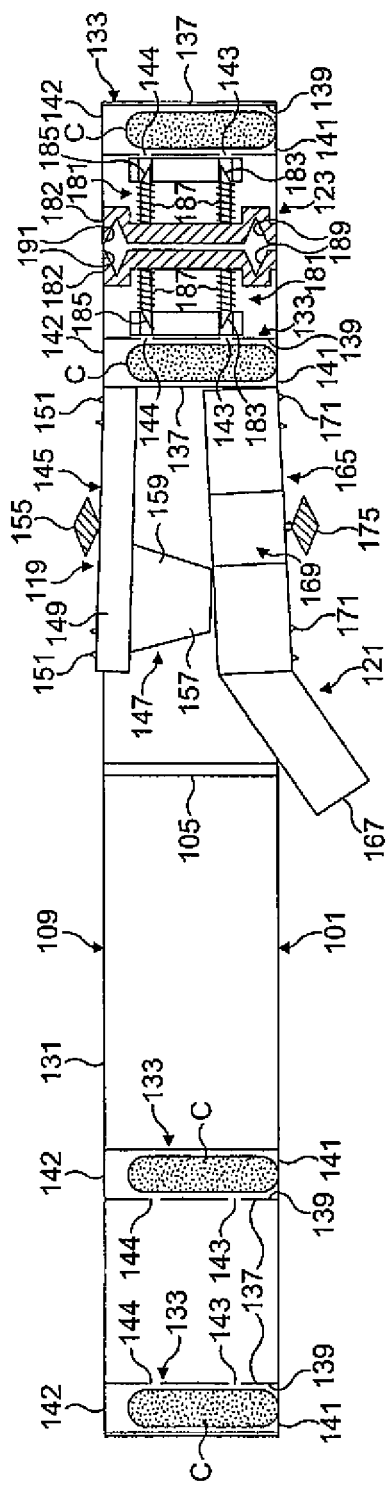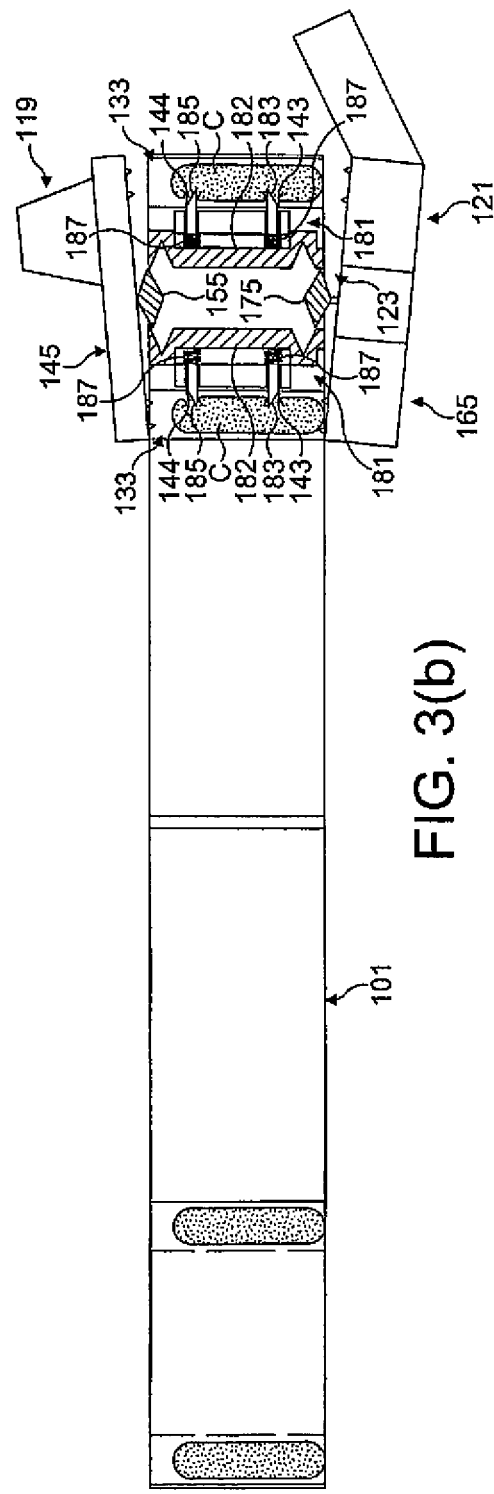
FIG. 3(a)
FIG. 3(b)

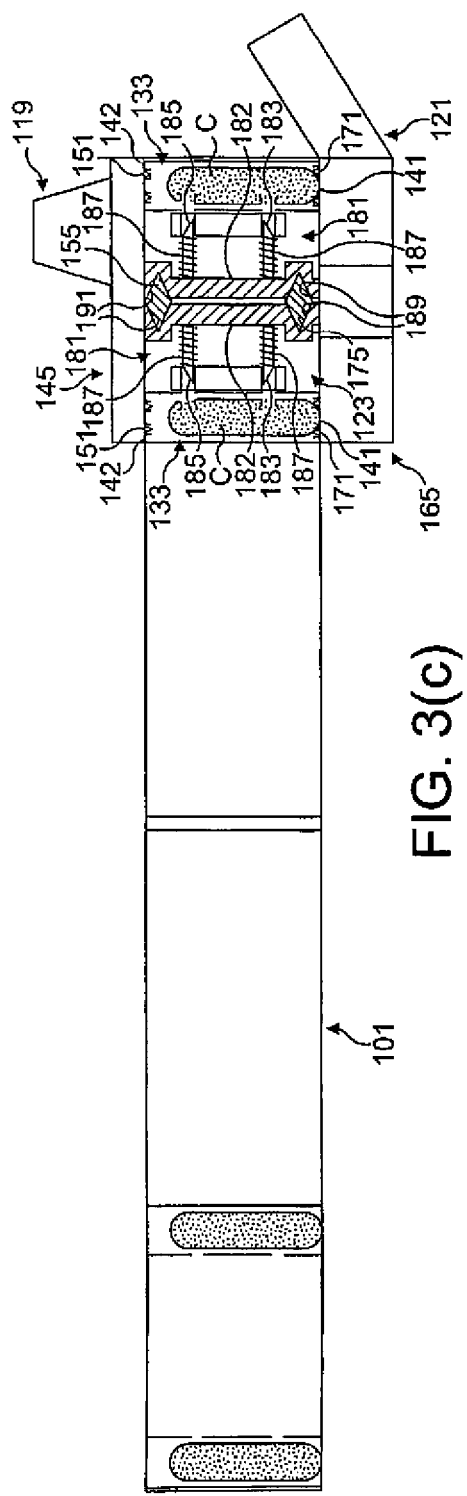
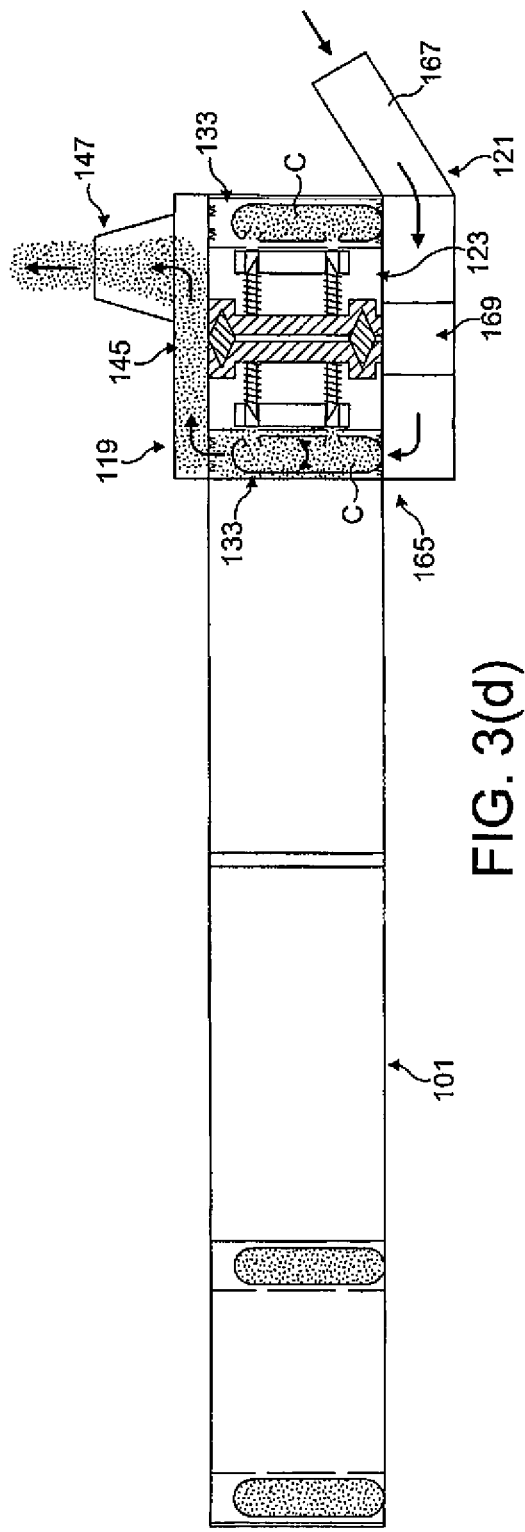

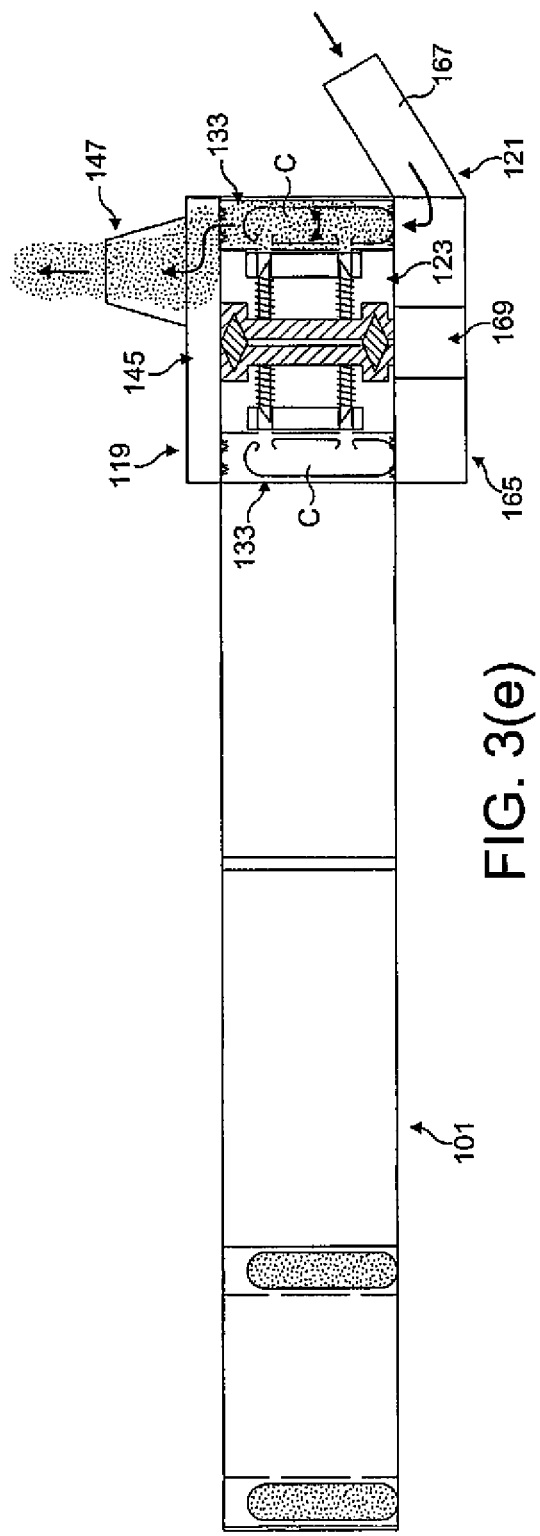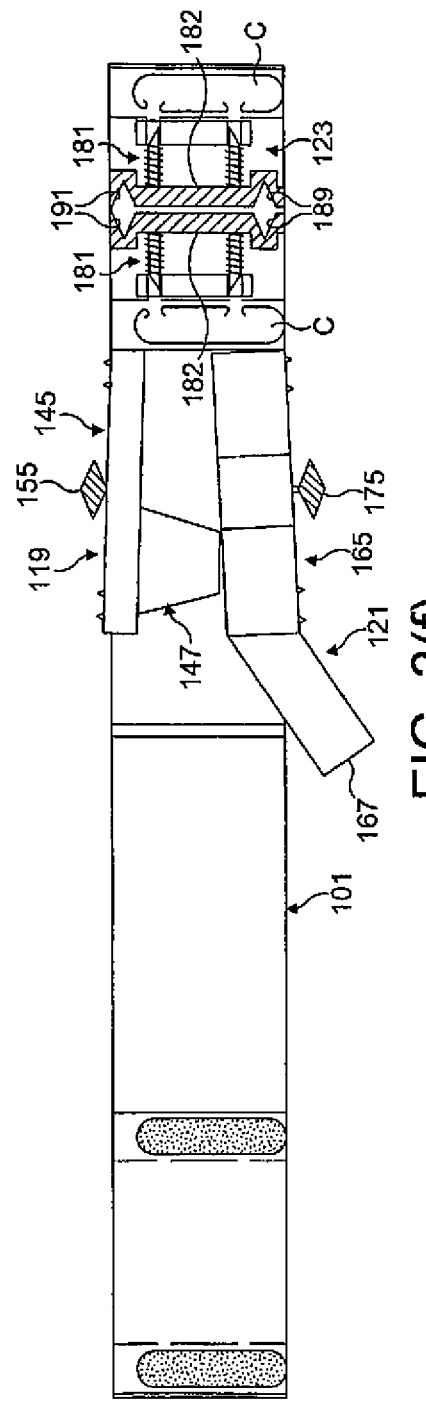

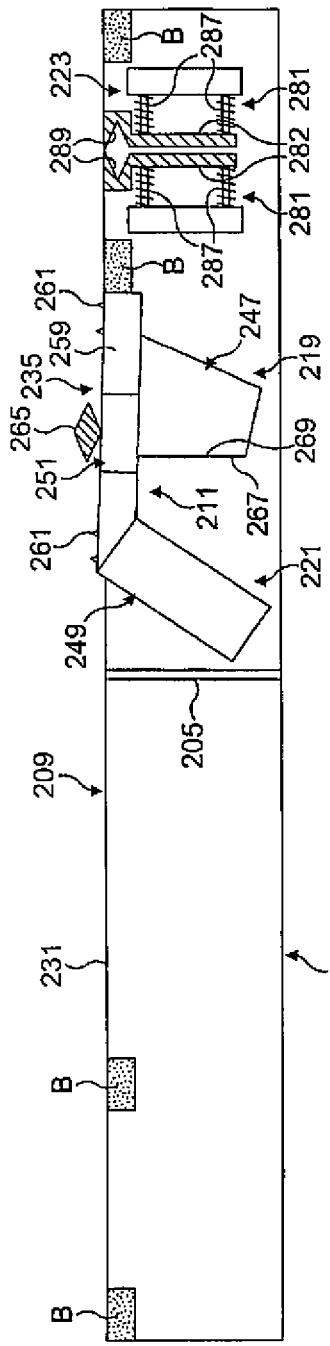
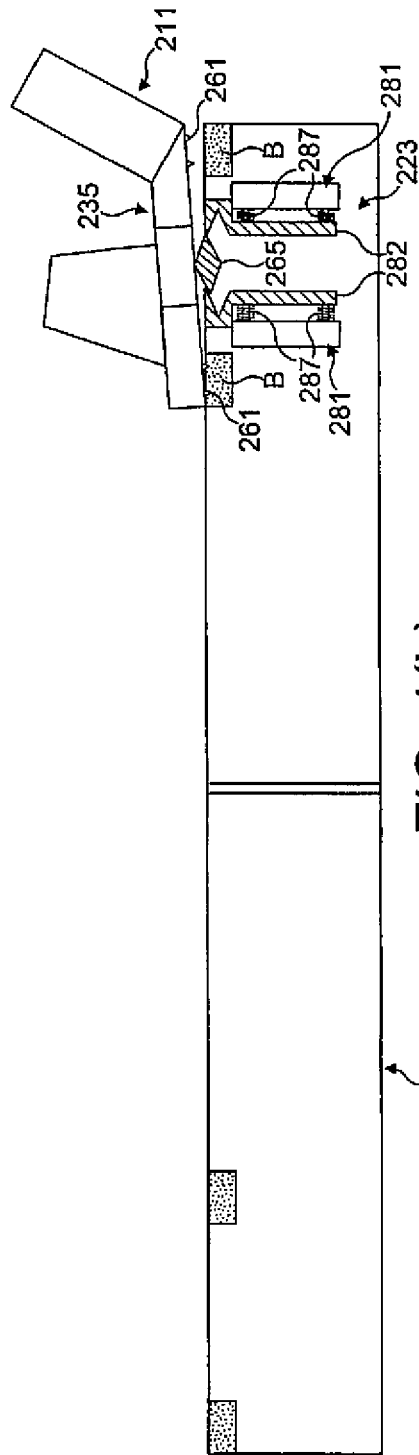
FIG. 4(a)
FIG. 4(b)

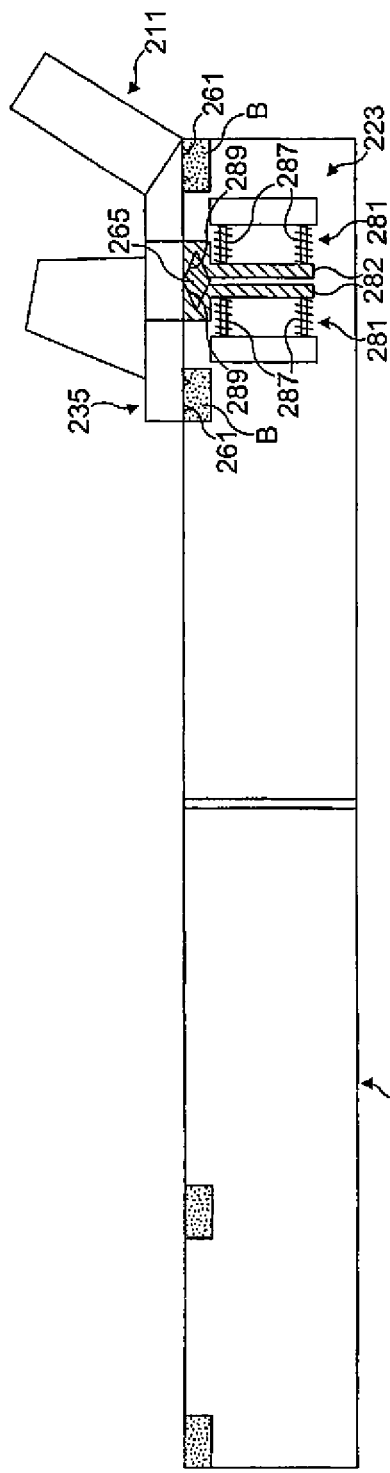
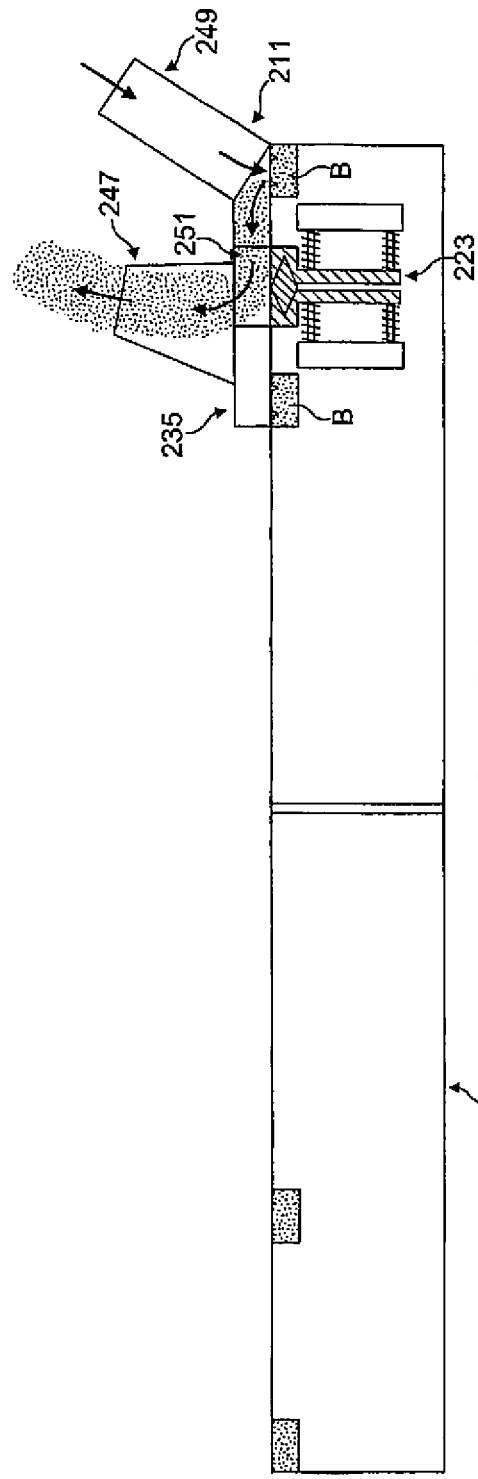

NASAL DELIVERY DEVICES

CROSS REFERENCE TO RELATED APPLICATIONS

This application is a continuation of U.S. patent application Ser. No. 14/058,647, filed on Oct. 21, 2013, which is a continuation of U.S. patent application Ser. No. 13/471,146, filed May 14, 2012, now U.S. Pat. No. 8,590,530, which is a continuation of U.S. patent application Ser. No. 11/663,099, now abandoned, filed Aug. 22, 2007, which is a National Phase Application of International Application No. PCT/GB2005/003549, filed on Sep. 15, 2005, which claims the benefit of and priority to UK patent application no. GB 0420513.4, filed on Sep. 15, 2004. The disclosures of the above applications are incorporated herein by reference in their entireties.

FIELD OF THE INVENTION

The present invention relates to nasal delivery devices and methods for delivering substances, in particular particulate substances, such as powdered substances, to the nasal cavities of subjects, and in particular multi-dose devices adapted for use with a plurality of containers, such as capsules, blisters and vials, which each contain a single dose of substance.

BACKGROUND OF THE INVENTION

Current nasal delivery systems can adequately treat topical diseases, but are not suited to the delivery of substances to the upper part of the nasal airway, and in particular for targeted delivery to the olfactory region and sinus ostia.

The Turbohaler® as developed by AstraZeneca AB, where adapted for nasal delivery has not been a success. A large fraction of particles is deposited in the anterior region of the nasal cavity. Furthermore, the nasal cavity becomes narrower during nasal inhalation, thus further reducing the deposition efficiency in the posterior regions of the nasal airway, in particular in narrow and congested noses. There is also a considerable risk of inhalation of small particles to the lungs, as demonstrated in previous studies.

SUMMARY OF THE INVENTION

It is thus an aim of the present invention to provide nasal delivery systems which are suited to deliver substances, in particular particulate substances, such as powdered substances, to the nasal cavities of subjects, and in particular nasal powder delivery systems for both topical delivery and nose-to-brain (N2B) delivery.

In one embodiment it is an aim of the present invention to provide for bi-directional nasal delivery using a single-dose or multi-dose device, such as a duo-dose device, where utilizing capsules or blisters containing active drug substance having a suitable particle size, size distribution, surface properties and formulations, in order to achieve optimal delivery to the nasal mucosa in general and/or targeted delivery to specific regions of a nasal cavity. Bi-directional nasal delivery is disclosed in the applicant's earlier WO-A-00/51672, the content of which is incorporated herein by reference.

In another embodiment it is an aim of the present invention to prevent delivery to selected regions of the nasal cavity, in particular to the anterior valve area, by utilizing two separate delivery channels, that is, a central channel for the drug substance and air, and an outer channel which acts to modify and optimize the deposition pattern of the particles in the nasal cavity.

In one aspect the present invention provides a nasal delivery device for delivering substance to a nasal cavity of a subject, the delivery device comprising: a container-receiving unit comprising a container chamber for receiving a substance-containing container which contains substance to be delivered to the nasal cavity of the subject, the container chamber including an inlet and an outlet; a nosepiece unit including a nosepiece for fitting to a nasal cavity of the subject and being in fluid communication with the outlet of the container chamber; a mouthpiece unit including a mouthpiece in fluid communication with the inlet of the container chamber and through which the subject in use exhales, such as to entrain substance from the container and deliver the same through the nosepiece; and moisture mitigation means for mitigating an effect of moisture in an exhaled breath on the entrainment of substance from the container, which means are provided, for example, by providing the container in a replaceable container-containing member, by a pressure-sensitive valve which normally closes the fluid connection between the container chamber and the mouthpiece, and a temperature regulator upstream of the container chamber.

In another aspect the present invention provides a nasal delivery device for delivering substance to a nasal cavity of a subject, the delivery device comprising: a container-receiving unit comprising a container chamber for receiving a substance-containing container which contains substance to be delivered to the nasal cavity of the subject, the container chamber including an inlet and an outlet; a nosepiece unit including a nosepiece for fitting to a nasal cavity of the subject and being in fluid communication with the outlet of the container chamber; a mouthpiece unit including a mouthpiece in fluid communication with the inlet of the container chamber and through which the subject in use exhales, such as to entrain substance from the container and deliver the same through the nosepiece; and a moisture-reducing element for reducing condensation at or downstream of the container chamber.

In a further aspect the present invention provides a nasal delivery device for delivering substance to a nasal cavity of a subject, the delivery device comprising: a container-receiving unit comprising a container chamber for receiving a substance-containing container which contains substance to be delivered to the nasal cavity of the subject, the container chamber including an inlet and an outlet; a nosepiece unit including a nosepiece for fitting to a nasal cavity of the subject and being in fluid communication with the outlet of the container chamber; a mouthpiece unit including a mouthpiece in fluid communication with the inlet of the container chamber and through which the subject in use exhales, such as to entrain substance from the container and deliver the same through the nosepiece.

In a yet further aspect the present invention provides a nasal delivery device for delivering substance to a nasal cavity of a subject, the delivery device comprising: a body member; a carrier which is supported by the body member and carries a plurality of substance-containing containers; a nosepiece unit including a nosepiece for fitting to a nasal cavity of the subject; a mouthpiece unit including a mouthpiece through which the subject in use exhales; and an actuating mechanism which is operative, in each operation, to open a plurality of the substance-containing containers, and including a valve unit for fluidly connecting the mouthpiece to a respective one of the opened substance-containing containers in successive exhalation cycles.

In a still further aspect the present invention provides a method of delivering substance to a nasal cavity of a subject, the method comprising the steps of: disposing a substance-containing container which contains substance to be delivered to the nasal cavity of the subject in a container chamber, the container chamber including an inlet and an outlet; fitting a nosepiece in fluid communication with the outlet of the container chamber to a nasal cavity of the subject; the subject exhaling through a mouthpiece which is in fluid communication with the inlet of the container chamber, such as to deliver an air flow through the container chamber and entrain substance from the container and deliver the same through the nosepiece and into the nasal cavity of the subject; and drawing moisture from the exhaled air flow upstream of the container chamber, such as to reduce condensation at or downstream of the container chamber.

In a yet still further aspect the present invention provides a method of delivering substance to a nasal cavity of a subject, the method comprising the steps of: disposing a substance-containing container which contains substance to be delivered to the nasal cavity of the subject in a container chamber, the container chamber including an inlet and an outlet; fitting a nosepiece in fluid communication with the outlet of the container chamber to a nasal cavity of the subject; and the subject exhaling through a mouthpiece which is in fluid communication with the inlet of the container chamber, such as to deliver an air flow through the container chamber and entrain substance from the container and deliver the same through the nosepiece and into the nasal cavity of the subject.

BRIEF DESCRIPTION OF THE DRAWINGS

Preferred embodiments of the present invention will now be described hereinbelow by way of example only with reference to the accompanying drawings, in which:

FIGS. 3(a) to (f) illustrate a nasal delivery device in accordance with a third embodiment of the present invention; and FIGS. 4(a) to (f) illustrate a nasal delivery device in accordance with a fourth embodiment of the present invention.

DETAILED DESCRIPTION OF THE INVENTION

Figure 1A:
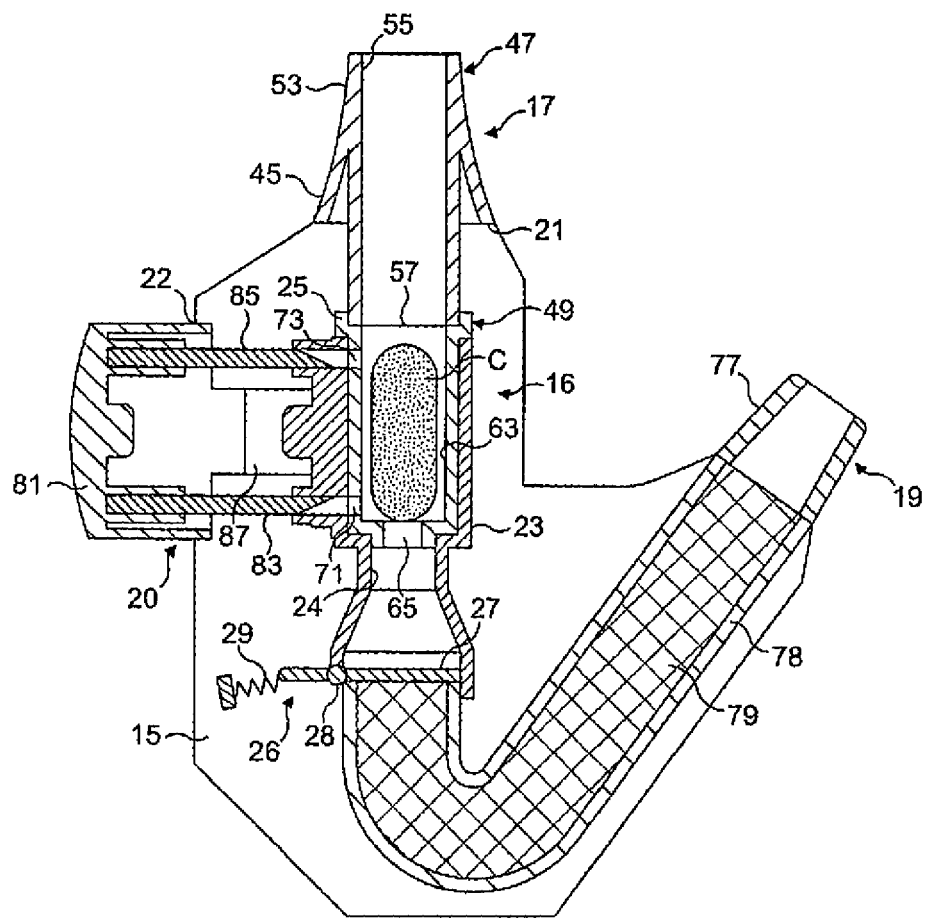
FIGS. 1 (a) to (f) illustrate a nasal delivery device in accordance with a first embodiment of the present invention.

The delivery device comprises a housing 15, a capsule-receiving unit 16 for receiving a capsule C, a nosepiece unit 17 for fitting to a nasal cavity of a subject, a mouthpiece unit 19 through which the subject exhales, and a capsule-piercing mechanism 20, which is operable to pierce a capsule C as contained by the capsule-receiving unit 16 and thereby prime the delivery device for operation, as will be described in more detail hereinbelow.

The housing 15 includes a first, nosepiece aperture 21, in this embodiment at the upper end of the housing 15, which receives the nosepiece unit 17, and a second, lateral aperture 22, in this embodiment in the lateral wall of the housing 15, through which extends an actuator button 81 of the capsule-piercing mechanism 20, as will be described in more detail hereinbelow.

The capsule-receiving unit 16 comprises a capsule-receiving member 23, in this embodiment an elongate, upstanding chamber which is disposed opposite the nosepiece aperture 21 in the housing 15, for receiving a capsule C, in this embodiment as contained within a capsule-containing member 49 of the nosepiece unit 17, as will be described in more detail hereinbelow.

In this embodiment the capsule-receiving member 23 includes an inlet 24 and an outlet 25 for providing for an air flow therethrough, with the outlet 25, as defined by an upper, downstream end of the capsule-receiving member 23, being adapted to receive the capsule-containing member 49 of the nosepiece unit 17, such that the capsule-containing member 49 is a sealing fit within the capsule-receiving member 23.

The capsule-receiving unit 16 further comprises a pressure-sensitive valve 26 in fluid communication with the inlet 24 of the capsule-receiving member 23, which is such as to prevent an air flow through the capsule-receiving member 23 until a predetermined pressure has been developed upstream thereof. In this embodiment the pressure-sensitive valve 26 is located at the inlet 24 to the capsule-receiving member 23.

In this embodiment the pressure-sensitive valve 26 comprises a flap member 27 which is hingeable about a pivot 28 and normally biased to a closed, sealing position by a resilient element 29, here a spring, such that a predetermined pressure is required to overcome the biasing force of the resilient element 29.

The nosepiece unit 17 comprises a main body member 45 which is configured to fit in the nosepiece aperture 21 of the housing 15, a nosepiece 47 which extends outwardly of the main body member 45 for fitting to the nostril of the subject, and a capsule-containing member 49 which extends inwardly of the main body member 45 and contains a capsule C, the contents of which are to be delivered to the nasal cavity of the subject. In this embodiment the capsule C is a conventional gelatine capsule which contains a particulate substance, such as a powdered substance, and typically a pharmaceutical substance.

In this embodiment the nosepiece 47 has a substantially frusta-conical outer section 53 for insertion into a nostril of the subject such as to provide a fluid-tight seal therewith, and includes an inner channel 55, here of substantially cylindrical section, through which substance is delivered to the nasal cavity of the subject. In this embodiment the nosepiece 47, in providing a fluid-tight seal with the nostril of the subject, provides for bi-directional delivery through the nasal airway of the subject, as disclosed in the applicant's earlier WO-A-00/51672. In another embodiment, however, the nosepiece 47 need not provide a sealing fit, thus encompassing delivery to the nasal cavity, but not necessarily bi-directional delivery.

In this embodiment the nosepiece 47 includes a trap element 57, typically a perforated or mesh element, for preventing any foreign matter, such as a part of the capsule C, which is above a predetermined size from passing through the nosepiece 47 and into the nasal cavity of the subject.

The capsule-containing member 49 includes an elongate flow passage 63, in this embodiment cylindrical in shape, in which the capsule C is oriented axially therealong such as to be rotatable therewithin when an air flow is delivered therethrough, and an inlet aperture 65 in fluid communication with one, the downstream, end of the flow passage 63, which inlet aperture 65 provides a flow restriction to an air flow as delivered therethrough and acts as a seat for one, the lower, end of the capsule C prior to the delivery of an air flow through the flow passage 63.

The capsule-containing member 49 further includes a plurality of, in this embodiment first and second piercing apertures 71, 73 in a lateral wall thereof for enabling the capsule C to be pierced at locations spaced along the axial length thereof. In this embodiment the first, lower aperture 71 is located such that the capsule C is pierced at a location above the height of the dose of substance as contained thereby when the lower end of the capsule C is seated in the inlet aperture 65 of the flow passage 63. In this way, the dose of substance as contained by the capsule C is not released into the flow passage 63 until an air flow is delivered through the flow passage 63.

In this embodiment the nosepiece unit 17 is provided as a replaceable unit which is replaced following each operation of the delivery device. In this embodiment the nosepiece unit 17 can be packaged in air-tight packaging, for example, an aluminum foil package.

In an alternative embodiment only the capsule-containing member 49 could be replaceable, such as to be replaceable following each operation, with the nosepiece 47 being a sealing fit to the other, downstream end of the capsule-containing member 49. In this embodiment the capsule-containing member 49 can be packaged in air-tight packaging, for example, an aluminum foil package.

In still another alternative embodiment the nosepiece unit 17 could be a re-useable unit, with the capsule-containing member 49 being separable from the nosepiece 47 to allow for replacement of the capsule C following operation of the delivery device. In this embodiment the capsule C can be packaged in air-tight packaging, for example, an aluminum foil package.

The mouthpiece unit 19 comprises a mouthpiece 77, in this embodiment as gripped in the lips of the subject, through which the subject exhales to deliver an entraining air flow through the capsule-receiving unit 16, and an air chamber 78, in this embodiment an elongate tubular section, which fluidly connects the mouthpiece 77 and the pressure-sensitive valve 26 of the capsule-receiving unit 16.

In this embodiment the air chamber 78 has a greater volume than the capsule-receiving member 23 of the capsule-receiving unit 16, and preferably has a volume at least twice that of the capsule-receiving member 23.

In this embodiment the air chamber 78 incorporates a temperature regulator 79, here formed as a condenser for cooling the exhaled air flow, at least at the upstream end thereof. With this configuration, the exhaled air flow is cooled during exhalation, and also a predetermined volume of cooler air, as contained by the air chamber 78, is available prior to release of the pressure-sensitive valve 26.

In this embodiment the temperature regulator 79 comprises a labyrinthine structure. In another embodiment the temperature regulator 79 could be provided by a filter element, which could also act as a microbiological filter.

In one embodiment the temperature regulator 79 could include means for drying the condensate as collected therein when the delivery device is not in use.

In one embodiment the air chamber 78 is removable, such as to allow for cleaning or replacement.

This arrangement has been found to provide for reliable operation of the delivery device, in delivering substance from the capsule C. The present inventors have established that the provision of moist exhaled air directly to the capsule C can sometimes prevent the required rotation of the capsule C, and thereby prevent proper release of the substance as contained thereby. By providing a volume of cooler air, and arranging for that volume of cooler air to be delivered initially in a burst, the required rotation of the capsule C is seen repeatedly.

Figure 1B:
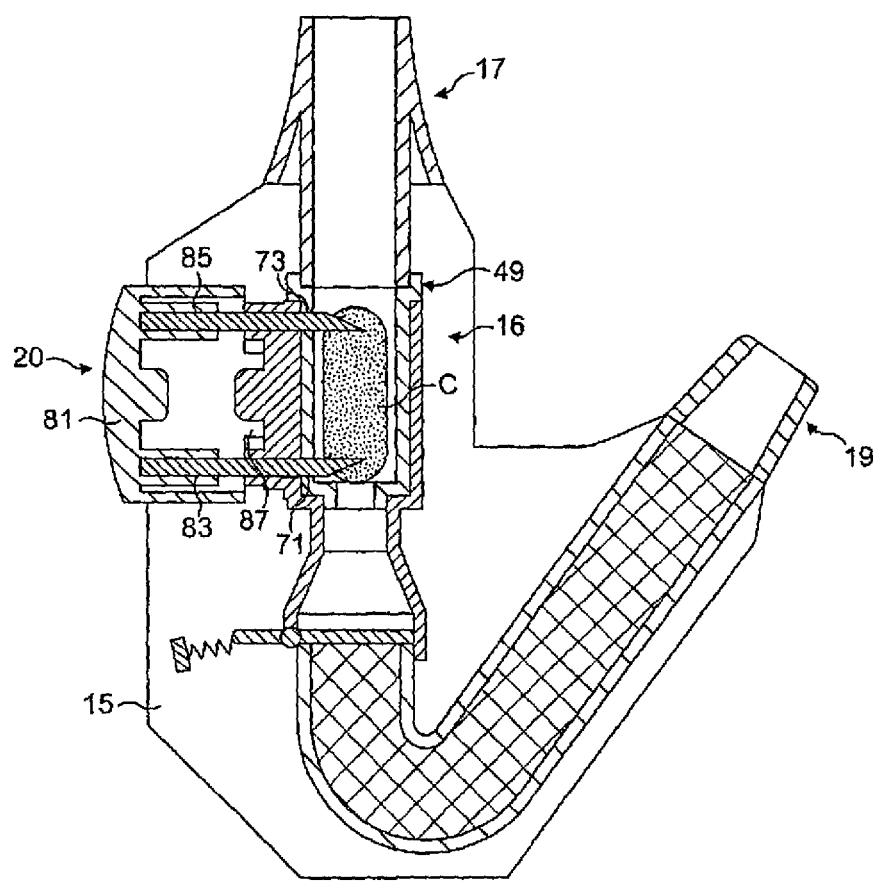
Figure 1C:
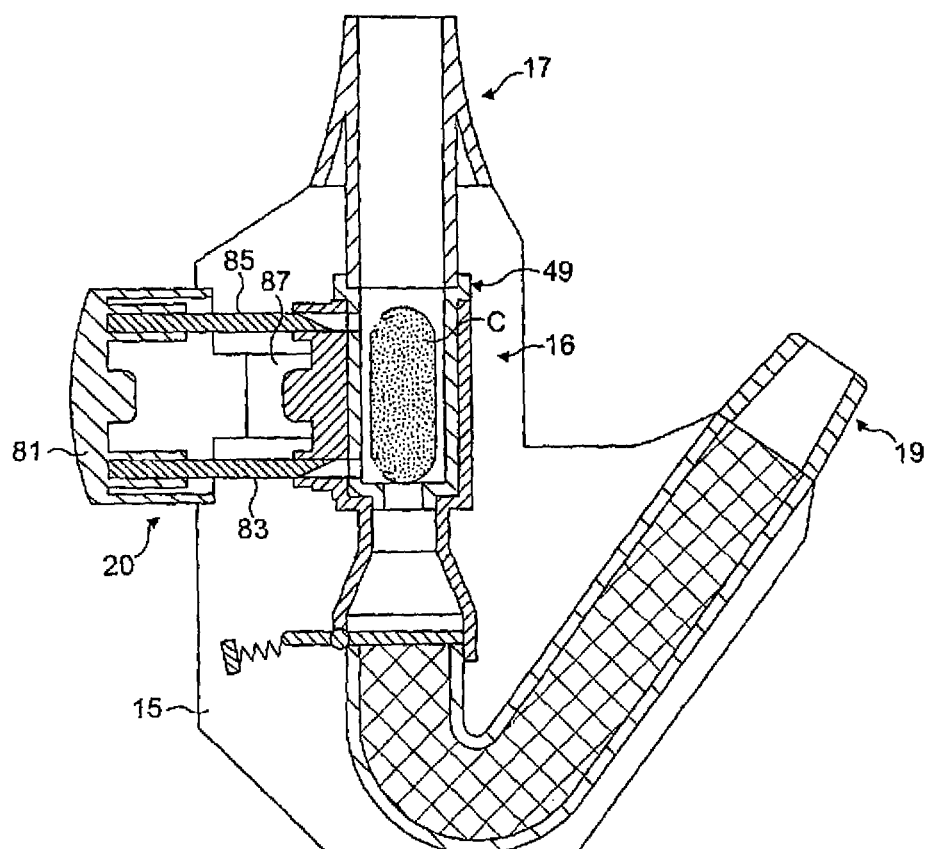
Figure 1D:
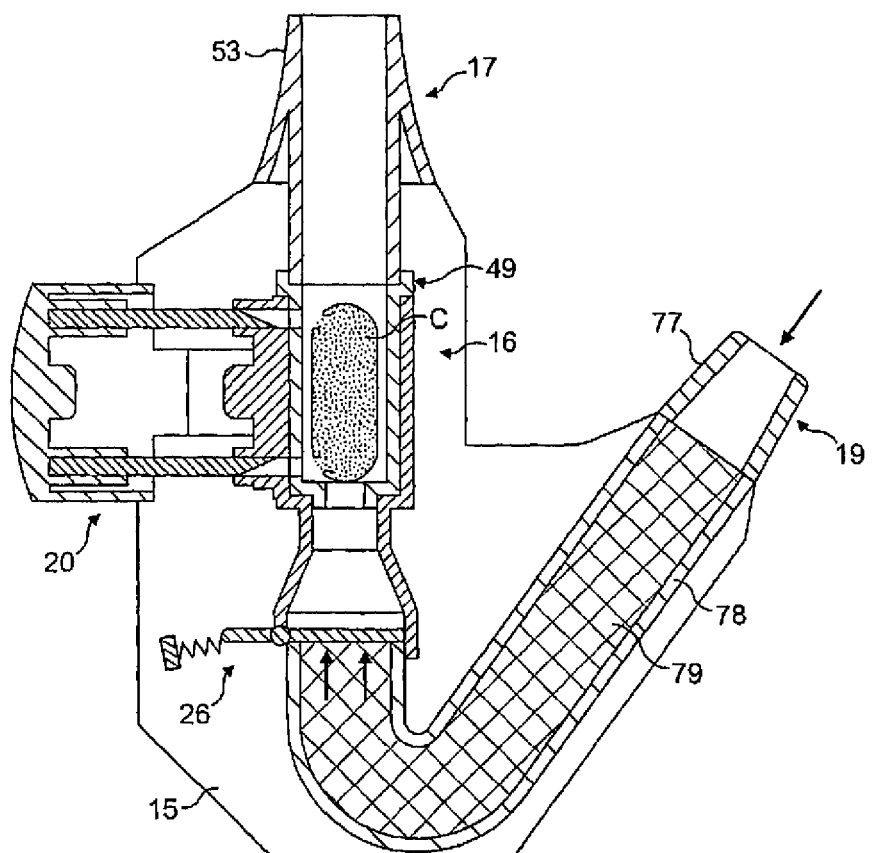
Figure 1E:
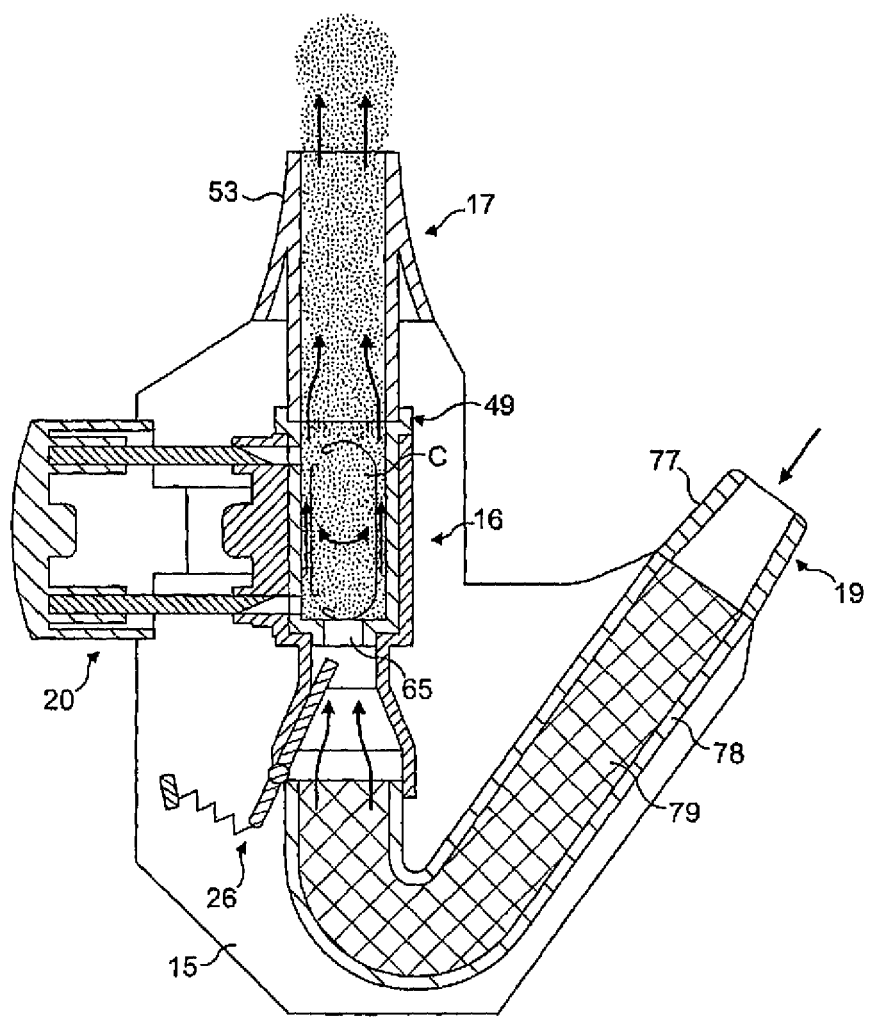
Figure 1F:
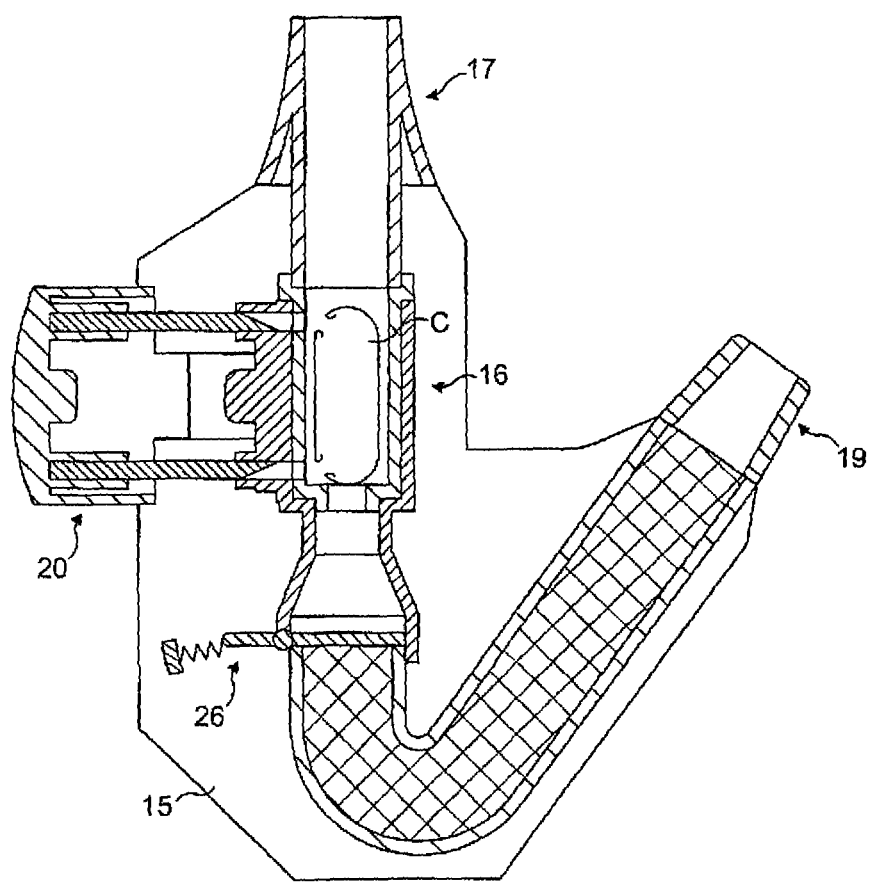

The capsule-piercing mechanism 20 comprises an actuator button 81 which extends through the lateral aperture 22 in the housing 15 such as to allow for operation by the subject, a plurality of, in this embodiment first and second piercing elements 83, 85 which are supported by the actuator button 81 and extend forwardly thereof, such that, on depression of the actuator button 81 from a retracted position, as illustrated in FIG. 1(*a*), to an extended position, as illustrated in FIG. 1(*b*), the piercing elements 83, 85 are driven through respective ones of the piercing apertures 71, 73 in the lateral wall of the capsule-containing member 49 to pierce the capsule C.

In this embodiment the capsule-piercing mechanism 20 includes a resilient element 87 which acts to bias the actuator button 81 outwardly towards the retracted position, such that, following depression of the actuator button 81 to pierce the capsule C, the actuator button 81 is returned to the retracted position. In this embodiment the resilient element 87 is formed as an integral part of the actuator button 81, but in other embodiments could be provided by a separate element, such as a compression spring.

Operation of the delivery device will now be described hereinbelow.

Firstly, taking the delivery device in hand, and with a nosepiece unit 17 inserted in the housing 15, as illustrated in FIG. 1(*a*), the subject depresses the actuator button 81 of the capsule-piercing mechanism 20 such as to pierce the capsule C as contained in the capsule-containing member 49, as illustrated in FIG. 1(*b*).

By depressing the actuator button 81, the capsule C is pierced by the piercing elements 83, 85 at two locations spaced along the axial length thereof. In this embodiment the first, lower piercing element 83 acts to pierce the capsule C at a location just above the height of the substance as contained by the capsule C, the capsule C only being part filled, and the second, upper piercing element 85 acts to pierce the upper, distal end of the capsule C.

The actuator button 81 is then released, which causes the actuator button 81 to be returned to the retracted under the bias of the biasing element 87, as illustrated in FIG. 1(*c*). In this way, the delivery device is primed and ready for use.

The subject then inserts the nosepiece 53 into one of his nostrils, grips the mouthpiece 77 in his or her lips and begins to exhale through the mouthpiece 77, as illustrated in FIG. 1(*d*). Initially, this exhalation is resisted by the pressure-sensitive valve 26, thereby preventing the delivery of an air flow through the capsule-containing member 49 and over the capsule C.

When the subject exhales with sufficient force to develop a pressure upstream of the pressure-sensitive valve 26 which is greater than a predetermined pressure, the pressure-sensitive valve 26 is opened, causing a sudden flow of air, as a burst of air, through the capsule-containing member 49, as illustrated in FIG. 1(*e*).

This burst of air acts to lift the capsule C from the seat as defined by the inlet aperture 65 of the capsule-containing member 49 and initiate the rotation of the capsule C, which rotation acts to release the substance from within the capsule C. With continued exhalation, the capsule C continues to rotate.

Following exhalation, as illustrated in FIG. 1(*f*), the pressure-sensitive valve 26 is returned to the closed, sealing position and the, now empty, capsule C is returned to a rest position.

This operation of the delivery device can be repeated with a new capsule C. As described hereinabove, in this embodiment the entire nosepiece unit 17 is replaced, but in other embodiments either the capsule-containing member 49 or just the capsule C could be replaced.

Figure 2A:
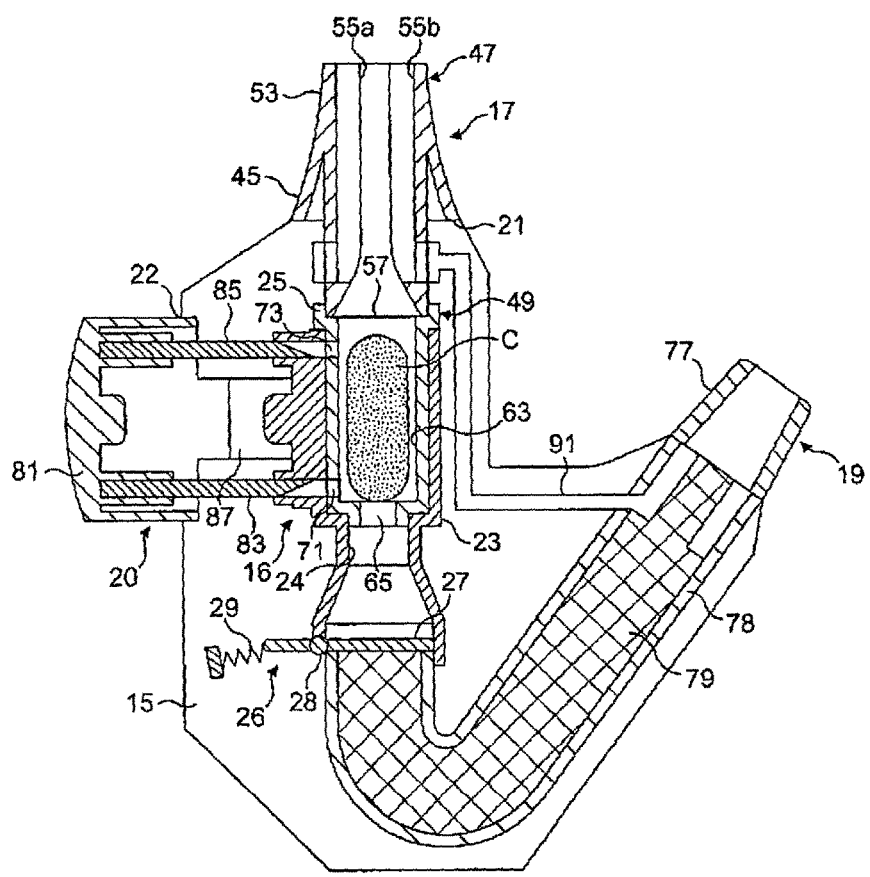
FIGS. 2(a) to (f) illustrate a nasal delivery device in accordance with a second embodiment of the present invention.
Figure 2B:
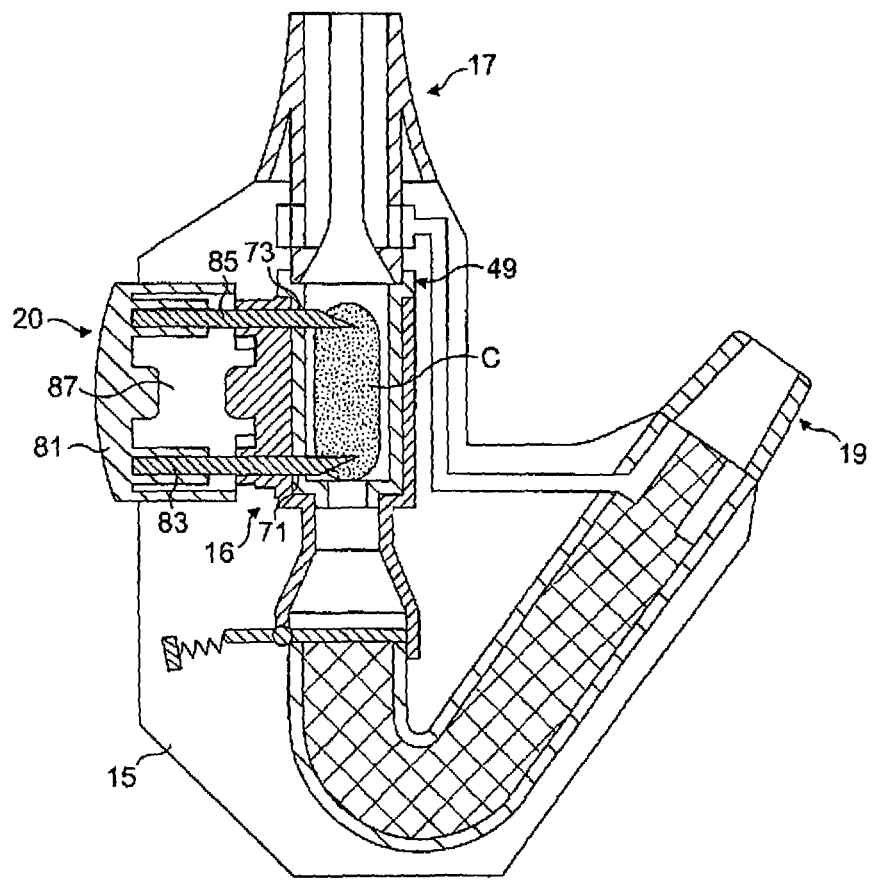
Figure 2C:
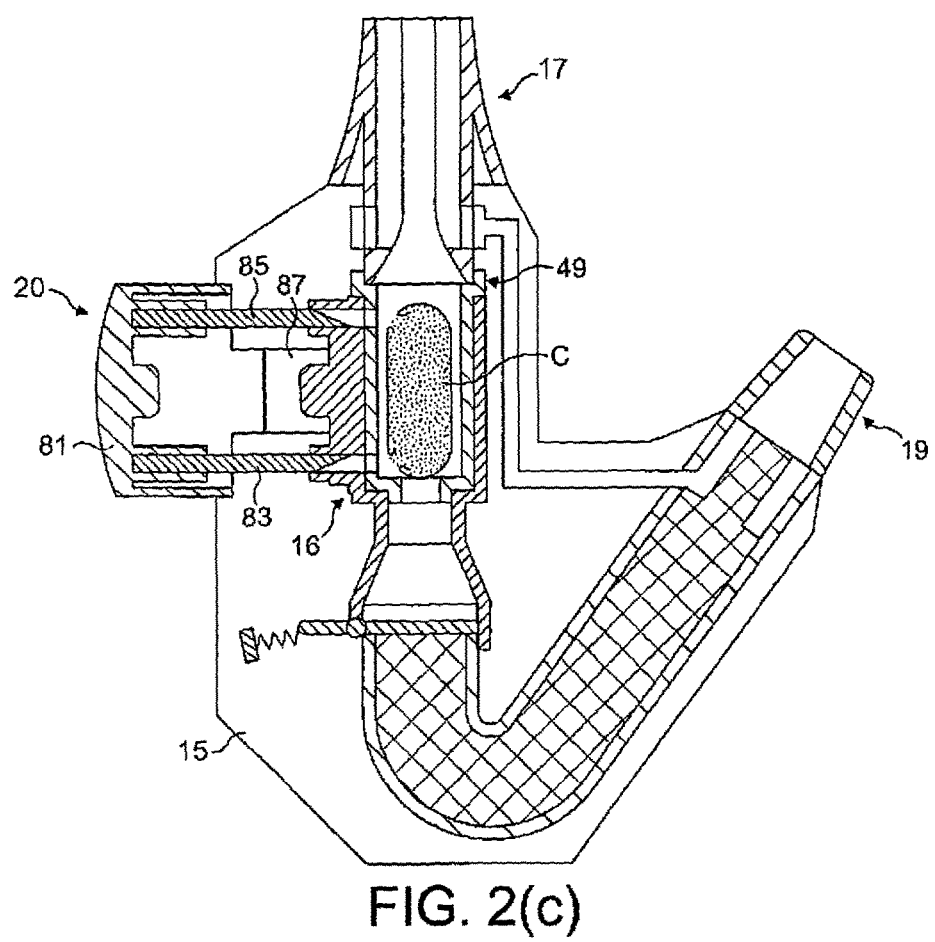
Figure 2D:
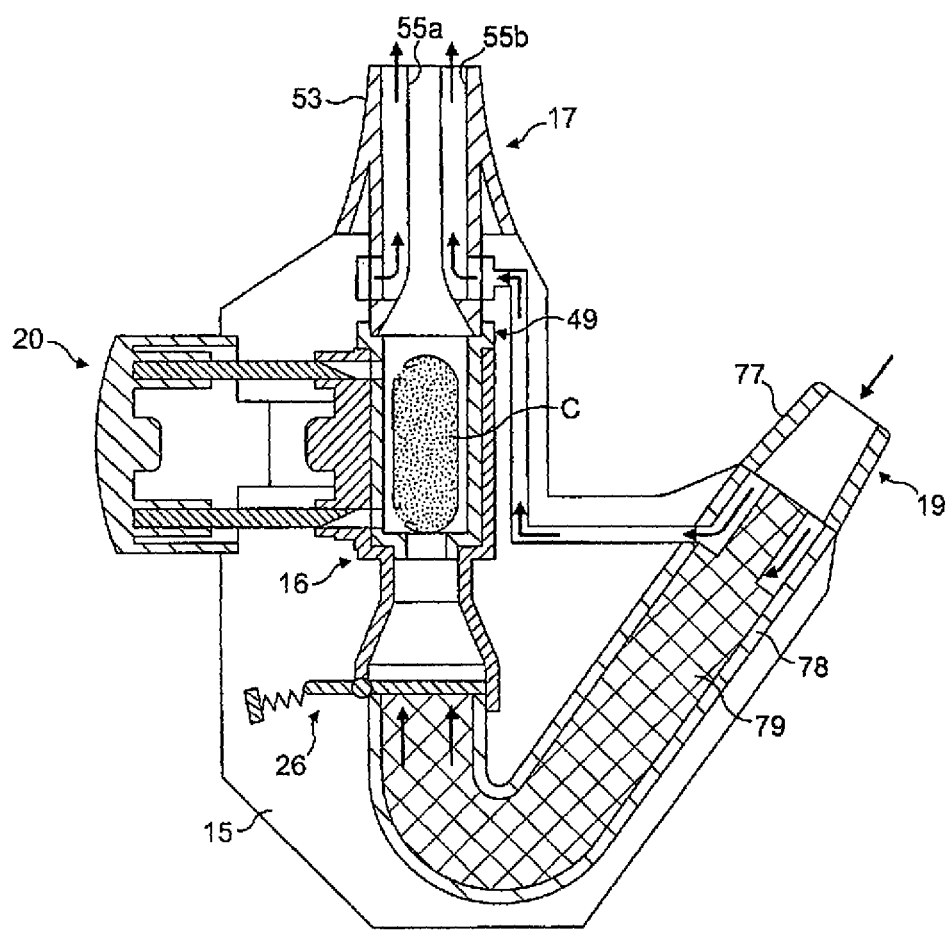
Figure 2E:
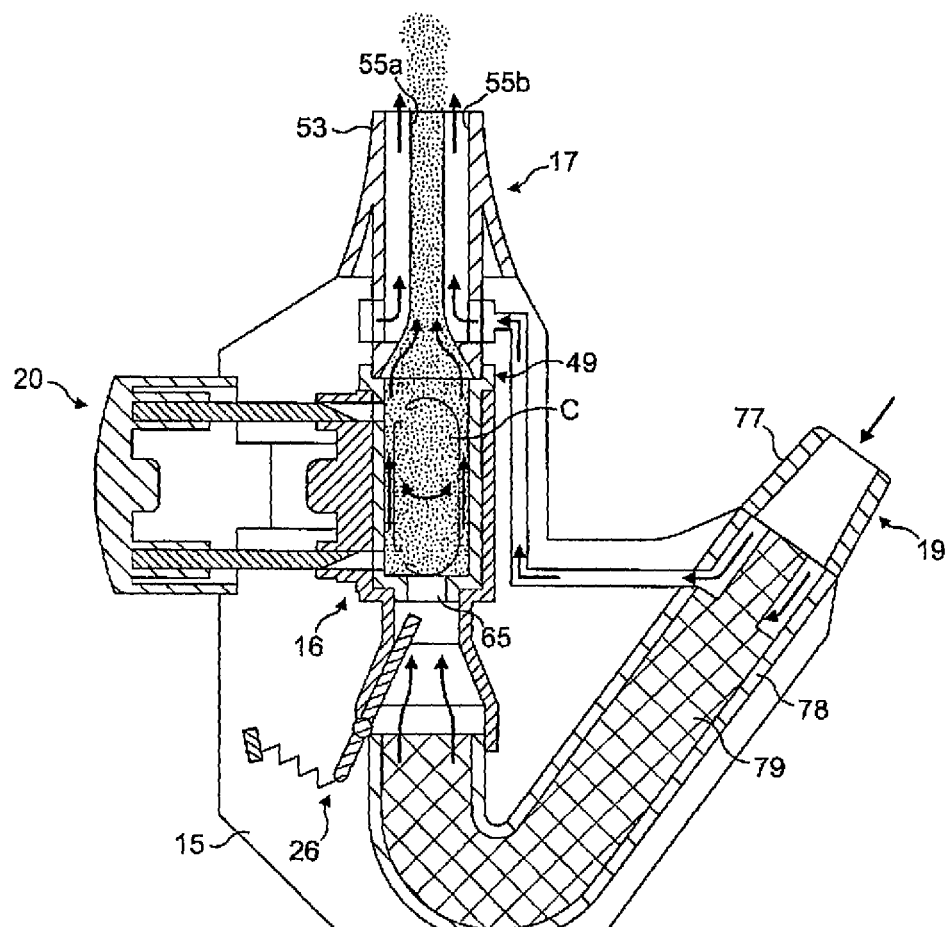
Figure 2F:
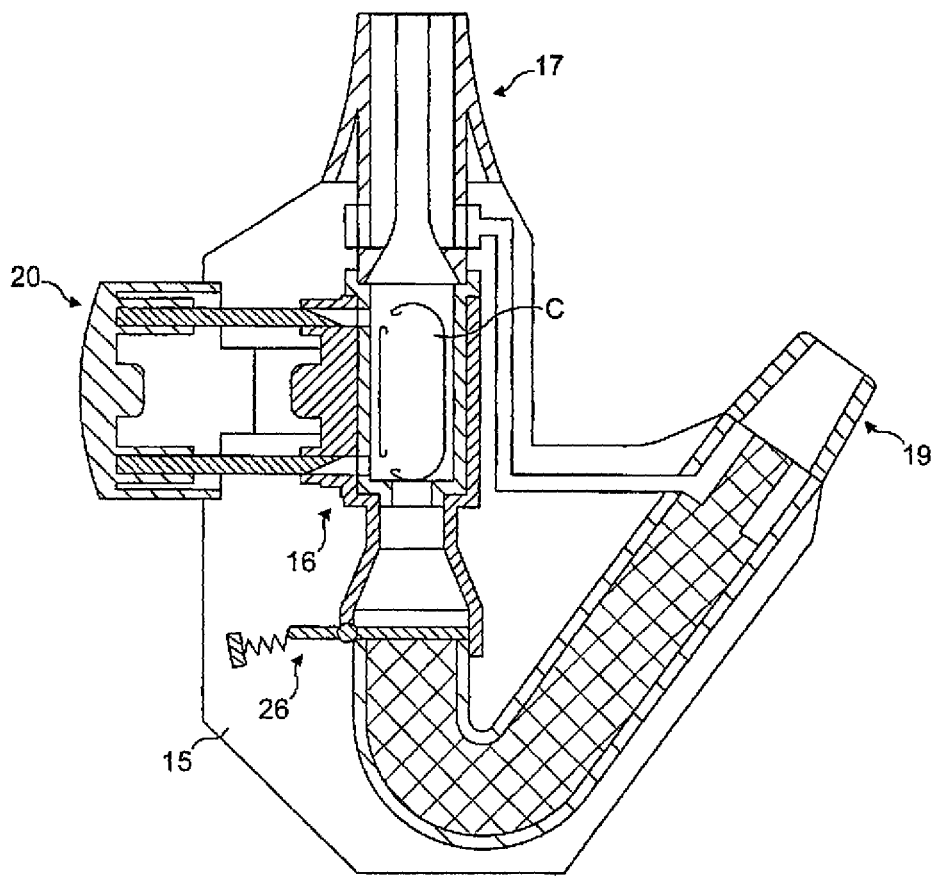

FIGS. 2(*a*) to (*f*) illustrate a nasal delivery device in accordance with a second embodiment of the present invention.

The delivery device of this embodiment is very similar to the delivery device of the above-described first embodiment, and thus, in order to avoid unnecessary duplication of description, only the differences will be described in detail.

The delivery device of this embodiment differs from that of the above-described embodiment in that the nosepiece 53 includes first and second channels 55*a*, 55*b*, in this embodiment concentric annular channels, which are centred about the longitudinal axis of the capsule-containing member 49, where the first, inner channel 55*a* is fluidly connected to the downstream end of the capsule-containing member 49 such that the substance as contained by the capsule C is delivered therethrough and the second, outer channel 55*b* is fluidly connected by a ducting channel 91 to the mouthpiece 77, in this embodiment upstream of the air chamber 78.

With this arrangement, a focussed powder aerosol is delivered from the outlet end of the inner channel 55*a*, and entrained by the co-axial air flow as delivered from the mouthpiece 77. This arrangement is particularly advantageous in targeting specific regions of the nasal airway, in particular posterior regions, such as the olfactory region. As this entraining air flow does not pass over the capsule C, the humidity of the entraining air flow is not significant.

FIGS. 3(*a*) to (*f*) illustrate a nasal delivery device in accordance with a third embodiment of the present invention.

The delivery device comprises a housing 101 which includes a central support spindle 105, a carrier 109 which carries a plurality of substance-containing capsules C, the contents of which are to be delivered to a nasal cavity of the subject, and is movably disposed to the housing 101, in this embodiment rotatably mounted to the housing 101 about the support spindle 105, a nosepiece unit 119 for fitting to a nasal cavity of a subject, a mouthpiece unit 121 through which the subject exhales, and a capsule-piercing mechanism 123, which is operable, in this embodiment simultaneously, to pierce a pair of capsules C and thereby prime the delivery device for operation, as will be described in more detail hereinbelow.

In this embodiment the capsules C are conventional gelatine capsules which contain a particulate substance, such as a powdered substance, and typically a pharmaceutical substance.

The carrier 109 comprises a body member 131, in this embodiment an annular element, and a plurality of capsule-containing members 133, each containing a capsule C, which are disposed symmetrically in adjacent pairs about the support spindle 105, such that, as the carrier 109 is indexed successively to new positions, new pairs of capsule-containing members 133 are indexed to the capsule-piercing mechanism 123.

In this embodiment the capsule-containing members 133 each comprise a tubular element 137 which defines an elongate flow passage 139, in this embodiment cylindrical in shape, in which the capsule C is oriented axially therealong such as to be rotatable therewithin when an air flow is delivered therethrough, and first and second sealing members 141, 142 which seal the opposite, lower and upper ends of the tubular element 137.

In this embodiment the capsule-containing members 133 each include a plurality of, in this embodiment first and second piercing apertures 143, 144 in a lateral wall thereof for enabling the capsule C to be pierced at locations spaced along the axial length thereof. In this embodiment the first, lower aperture 143 is located such that the capsule C is pierced at a location above the height of the dose of substance as contained thereby. In this way, the dose of substance as contained by the capsule C is not released into the flow passage 139 until an air flow is delivered through the flow passage 139.

The nosepiece unit 119 comprises a body member 145 which is movably, in this embodiment pivotally, coupled to the housing 101 such as to be movable between a first, inoperative position, as illustrated in FIG. 3(*a*), in which the nosepiece unit 119 is stowed away and a second, operative position, as illustrated in FIG. 3(*c*), and a nosepiece 147 which extends outwardly of the body member 145 for fitting to a nostril of the subject.

In this embodiment the body member 145 includes a flow channel 149 which fluidly connects the flow passages 139 of an adjacent pair of the capsule-containing members 133 to the nosepiece 147 when the nosepiece unit 119 is in the operative position.

In this embodiment the body member 145 includes first and second cutters 151 which are adapted to cut the upper scaling members 142 of the adjacent pair of capsule-containing members 133 when the nosepiece unit 119 is in the operative position.

In this embodiment the body member 145 includes a catch member 155, here having a diamond-shaped cross section which presents forwardly-directed, tapering surfaces when the nosepiece unit 119 is pivoted in either sense from or to the operative position, which acts to operate in part the capsule-piercing mechanism 123 and also latch the nosepiece unit 119 in the operative position, as will be described in more detail hereinbelow.

In this embodiment the nosepiece 147 has a substantially frusta-conical outer section 157 for insertion into a nostril of the subject such as to provide a fluid-tight seal therewith, and includes an inner channel 159 through which substance is delivered to the nasal cavity of the subject. In this embodiment the nosepiece 147, in providing a fluid-tight seal with the nostril of the subject, provides for bi-directional delivery through the nasal airway of the subject, as disclosed in the applicant's earlier WO-A-00/51672. In another embodiment, however, the nosepiece 147 need not provide a sealing fit, thus encompassing delivery to the nasal cavity, but not necessarily bi-directional delivery.

The mouthpiece unit 121 comprises a body member 165 which is movably, in this embodiment pivotally, coupled to the housing 101 such as to be movable between a first, inoperative position, as illustrated in FIG. 3(*a*), in which the mouthpiece unit 121 is stowed away and a second, operative position, as illustrated in FIG. 3(*c*), a mouthpiece 167 which extends outwardly of the body member 165, in this embodiment as gripped in the lips of the subject, through which the subject exhales to deliver an entraining air flow, and a valve unit 169 which is operative fluidly to connect the mouthpiece 167 to a respective one of the adjacent pair of opened capsule-containing members 133 in successive exhalation cycles.

In this embodiment the valve unit 169 comprises a pressure sensor which is operative to detect the pressure as developed in the mouthpiece 167 and an electro-mechanical valve, which includes two flow channels and is switchable such as fluidly to connect the mouthpiece 167 first to one of the pair of capsule-containing members 133 and, following the first exhalation cycle, which is represented by a return to ambient pressure, then to the other of the pair of capsule-containing members 133.

In this embodiment the body member 165 includes first and second cutters 171 which are adapted to cut the lower sealing members 141 of the adjacent pair of capsule-containing members 133 when the mouthpiece unit 121 is in the operative position.

In this embodiment the body member 165 includes a catch member 175, here having a diamond-shaped cross section which presents forwardly-directed, tapering surfaces when the mouthpiece unit 121 is pivoted in either sense from or to the operative position, which acts to operate in part the capsule-piercing mechanism 123 and also latch the mouthpiece unit 121 in the operative position, as will be described in more detail hereinbelow.

The capsule-piercing mechanism 123 comprises first and second piercing units 181, which are disposed in opposed, back-to-back relation and are actuated by movement of the nosepiece unit 119 and the mouthpiece unit 121 from the inoperative, stowed positions to the operative positions.

Each of the piercing units 181 includes an actuator button 182 and a plurality of, in this embodiment first and second piercing elements 183, 185 which are supported by the actuator button 182 and extend forwardly thereof, such that, on depression of the actuator button 182 from a retracted position, as illustrated in FIG. 3(*a*), to an extended position, as illustrated in FIG. 3(*b*), the piercing elements 183, 185 are driven through respective ones of the piercing apertures 143, 144 in the lateral wall of the respective capsule-containing member 133 to pierce the capsule C.

In this embodiment the capsule-piercing units 181 each include a resilient element 187 which acts to bias the respective actuator button 182 inwardly towards the retracted position, such that, following depression of the actuator button 182 to pierce the capsule C, the actuator button 182 is returned to the retracted position.

In this embodiment the actuator buttons 182 each include first and second recesses 189, 191 in a rear surface thereof, here V-shaped in cross section, which are configured such as to engage respective ones of the catches 155, 175 on the body members 145, 165 of the nosepiece and mouthpiece units 119, 121, such as to latch the same in the operative positions.

Operation of the delivery device will now be described hereinbelow.

Firstly, the subject indexes the carrier 109 such as to present the next pair of capsule-containing members 133 at the capsule-piercing mechanism 123, as illustrated in FIG. 3(*a*).

The subject then moves the nosepiece unit 119 and the mouthpiece unit 121 to the respective operative positions, in this embodiment by pivoting the same relative to the housing 101, as illustrated in FIGS. 3(*b*) and (*c*).

In moving the nosepiece unit 119 and the mouthpiece unit 121 to the respective operative positions, the catch member 155 on the body member 145 of the nosepiece unit 119 and the catch member 175 on the body member 165 of the mouthpiece unit 121 engage between the respective ends of the opposing actuator buttons 182 of the piercing units 181, such as to bias the actuator buttons 182 outwardly and pierce the capsules C as contained in the capsule-containing members 133, as illustrated in FIG. 3(*b*).

By depressing the actuator buttons 182, the capsules C are pierced by the piercing elements 183, 185 at two locations spaced along the axial length thereof, with the piercing elements 183, 185 extending through the piercing apertures 143, 144 in the lateral walls of the tubular elements 137 of the capsule-containing members 133. In this embodiment the first, lower piercing elements 183 act to pierce the capsules C at locations just above the height of the substance as contained by the capsules C, the capsules C only being part filled, and the second, upper piercing elements 185 act to pierce the upper, distal ends of the capsules C.

On further moving the nosepiece unit 119 and the mouthpiece unit 121 to the respective operative positions, the catch member 155 on the body member 145 of the nosepiece unit 119 and the catch member 175 on the body member 165 of the mouthpiece unit 121 engage in the respective recesses 189, 191 in the rear surfaces of the opposing actuator buttons 182 of the piercing units 181, as illustrated in FIG. 3(*c*), with the actuator buttons 182 being returned to the retracted positions under the bias of the biasing elements 187, whereby the nosepiece unit 119 and the mouthpiece unit 121 are latched in the operative positions.

Also, with movement of the nosepiece unit 119 and the mouthpiece unit 121 to the operative positions, the cutters 151 on the body member 145 of the nosepiece unit 119 act to rupture the upper sealing members 142 of the capsule-containing members 133 and the cutters 171 on the body member 165 of the mouthpiece unit 121 act to rupture the lower sealing members 141 of the capsule-containing members 133.

The subject then inserts the nosepiece 147 into one of his or her nostrils, grips the mouthpiece 167 in his or her lips and exhales through the mouthpiece 167, as illustrated in FIG. 3(*d*).

In this first exhalation cycle, the valve unit 169 is configured such as to direct the exhaled air flow through one of the pair of capsule-containing members 133, which air flow acts to lift the capsule C and cause rotation of the capsule C, and which rotation acts to release the substance from within the capsule C. With continued exhalation, the capsule C continues to rotate.

Following exhalation, the, now empty, capsule C returns to a rest position, and, as detected by the absence of any pressure in the mouthpiece 167, the valve unit 169 is re-configured such that the mouthpiece 167 is fluidly connected to the other of the pair of capsule-containing members 133, whereby the air flow as developed by a subsequent exhalation breath is directed through the other of the pair of capsule-containing members 133.

In one mode of operation the nosepiece 147 is inserted in the other of the nostrils of the subject, and the subject grips the mouthpiece 167 in his or her lips and exhales through the mouthpiece 167, as illustrated in FIG. 3(*e*).

In this second, subsequent exhalation cycle, the valve unit 169 is configured such as to direct the exhaled air flow through the other of the pair of capsule-containing members 133, which air flow acts to lift the capsule C and cause rotation of the capsule C, and which rotation acts to release the substance from within the capsule C. With continued exhalation, the capsule C continues to rotate.

In this mode of operation the same, or indeed different, substances can be delivered to each of the nasal cavities of the subject.

Following exhalation, the, now empty, capsule C returns to a rest position.

In another mode of operation, where the capsules C in the pair of capsule-containing members 133 contain different substances, and these substances are both to be delivered to one nasal cavity, the nosepiece 147 is not moved to the other nostril of the subject.

Following use of the delivery device, the nosepiece unit 119 and the mouthpiece unit 121 are returned to the respective stowed, inoperative positions, in this embodiment by pivoting the same relative to the housing 101, as illustrated in FIG. 3(f).

In moving the nosepiece unit 119 and the mouthpiece unit 121 to the respective inoperative positions, the catch member 155 on the body member 145 of the nosepiece unit 119 and the catch member 175 on the body member 165 of the mouthpiece unit 121 are released from engagement with the recesses 189, 191 in the rear surfaces of the opposing actuator buttons 182 of the piercing units 181.

This operation of the delivery device can then subsequently be repeated for the next pair of capsules C.

Figure 4E:
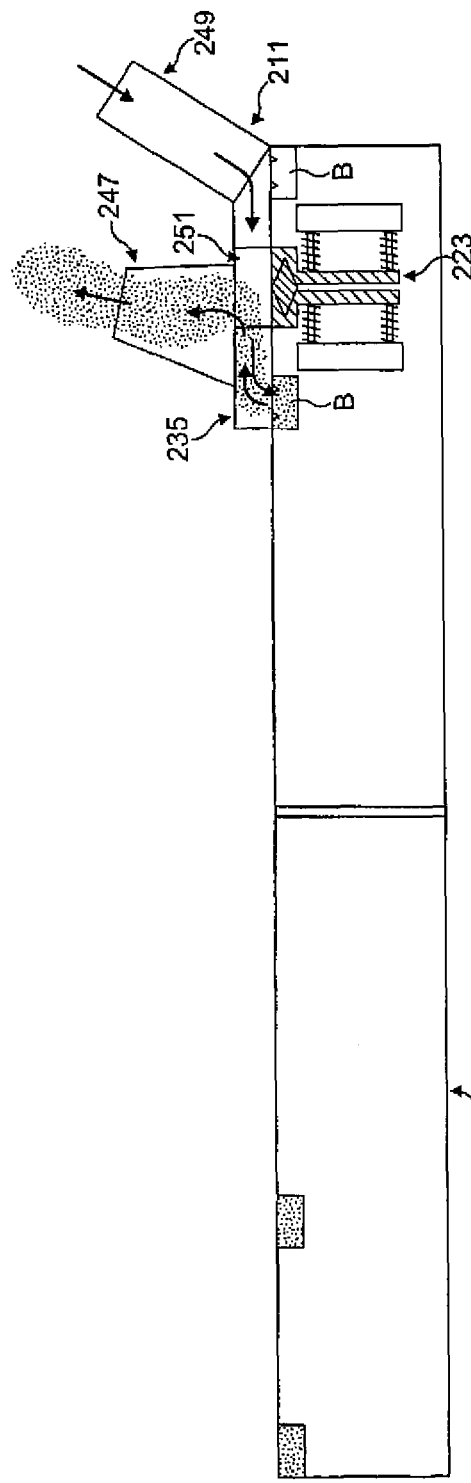
Figure 4F:
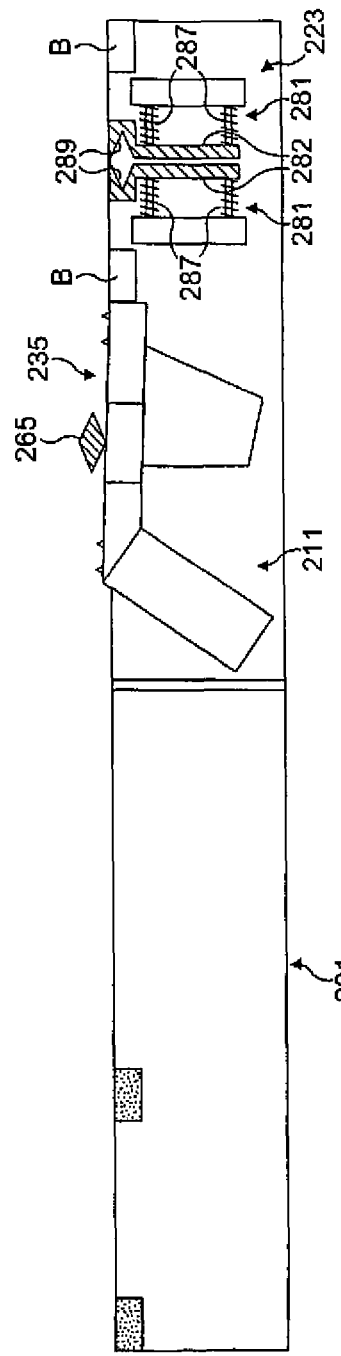

FIGS. 4(a) to (f) illustrate a nasal delivery device in accordance with a fourth embodiment of the present invention.

The delivery device comprises a housing 201 which includes a central support spindle 205, a carrier 209 which carries a plurality of substance-containing blisters B, the contents of which are to be delivered to a nasal cavity of the subject, and is movably disposed to the housing 201, in this embodiment rotatably mounted to the housing 201 about the support spindle 205, an interface assembly 211 which provides the interface to the subject, and a latch mechanism 223 which acts to latch the interface assembly 211 in the operative position, as will be described in more detail hereinbelow.

In this embodiment the blisters B are conventional blisters which contain a particulate substance, such as a powdered substance, and typically a pharmaceutical substance.

The carrier 209 comprises a body member 231, in this embodiment an annular element, and a plurality of blisters B which are disposed symmetrically in adjacent pairs about the support spindle 205, such that, as the carrier 209 is indexed successively to new positions, new pairs of blisters B are indexed to the operative position of the interface assembly 211.

The interface assembly 211 comprises a body member 235 which is movably, in this embodiment pivotally, coupled to the housing 201 such as to be movable between a first, inoperative position, as illustrated in FIG. 4(a), in which the interface assembly 211 is stowed away and a second, operative position, as illustrated in FIG. 4(c), a nosepiece unit 219 which includes a nosepiece 247 which extends outwardly of the body member 235 for fitting to a nostril of the subject, a mouthpiece unit 221 which includes a mouthpiece 249 which extends outwardly of the body member 235, in this embodiment as gripped in the lips of the subject, through which the subject exhales to deliver an entraining air flow, and a valve unit 251 which is operative fluidly to connect the mouthpiece 249 to a respective one of the adjacent pair of opened blisters B in successive exhalation cycles.

In this embodiment the body member 235 includes a flow channel 259 which fluidly connects the adjacent pair of blisters B to the nosepiece 249 when the interface assembly 211 is in the operative position.

In this embodiment the body member 235 includes first and second cutters 261 which are adapted to cut the sealing members of the adjacent pair of blisters B when the interface assembly 211 is in the operative position.

In this embodiment the body member 235 includes a catch member 265, here having a diamond-shaped cross section which presents forwardly-directed, tapering surfaces when the interface assembly 211 is pivoted in either sense from or to the operative position, which acts to latch the interface assembly 211 in the operative position, as will be described in more detail hereinbelow.

In this embodiment the nosepiece 247 has a substantially frusta-conical outer section 267 for insertion into a nostril of the subject such as to provide a fluid-tight seal therewith, and includes an inner channel 269 through which substance is delivered to the nasal cavity of the subject. In this embodiment the nosepiece 247, in providing a fluid-tight seal with the nostril of the subject, provides for bi-directional delivery through the nasal airway of the subject, as disclosed in the applicant's earlier WO-A-00/51672. In another embodiment, however, the nosepiece 247 need not provide a sealing fit, thus encompassing delivery to the nasal cavity, but not necessarily bi-directional delivery.

In this embodiment the valve unit 251 comprises a pressure sensor which is operative to detect the pressure as developed in the mouthpiece 249 and an electro-mechanical valve, which includes two flow channels and is switchable such as fluidly to connect the mouthpiece 249 first to one of the pair of blisters B and, following the first exhalation cycle, which is represented by a return to ambient pressure, then to the other of the pair of blisters B.

The latch mechanism 223 comprises first and second latch elements 281, which are disposed in opposed, back-to-back relation, and each comprise a latch body 282 and a resilient element 287 which acts to bias the latch body 282 forwardly to a latching position.

In this embodiment the latch bodies 282 each include a recess 289 in a rear surface thereof, here V-shaped in cross section, which acts to engage the catch 265 on the body member 235 of the interface assembly 211 when the interface assembly 211 is in the operative position.

Operation of the delivery device will now be described hereinbelow.

Firstly, the subject indexes the carrier 209 such as to present the next pair of blisters B at the operative position of the interface assembly 211, as illustrated in FIG. 4(a).

The subject then moves the interface assembly 211 to the operative position, in this embodiment by pivoting the same relative to the housing 201, as illustrated in FIGS. 4(b) and (c).

In moving the interface assembly 211 to the operative position, the catch member 265 on the body member 235 of the interface assembly 211 engages between the respective ends of the latch bodies 282 of the latch units 281, such as to bias the latch bodies 282 outwardly, as illustrated in FIG. 4(b).

On further moving the interface assembly 211 to the operative position, the catch member 265 on the body member 235 of the interface assembly 211 engages in the respective recesses 289 in the rear surfaces of the opposing latch bodies 282 of the latch units 281, as illustrated in FIG. 4(c), with the latch bodies 282 being returned to the retracted positions under the bias of the biasing elements 287, whereby the interface assembly 211 is latched in the operative position.

Also, with movement of the interface assembly 211 to the operative position, the cutters 261 on the body member 235 of the interface assembly 211 act to rupture the sealing members of the adjacent pair of blisters B.

The subject then inserts the nosepiece 247 into one of his or her nostrils, grips the mouthpiece 249 in his or her lips and exhales through the mouthpiece 249, as illustrated in FIG. 4(*d*).

In this first exhalation cycle, the valve unit 251 is configured such as to direct the exhaled air flow through one of the pair of blisters B, which air flow acts to entrain the substance from the blister B.

Following exhalation, the blister B is emptied, and, as detected by the absence of any pressure in the mouthpiece 249, the valve unit 251 is re-configured such that the mouthpiece 249 is fluidly connected to the other of the pair of blisters B, whereby the air flow as developed by a subsequent exhalation breath is directed through the other of the pair of blisters B.

In one mode of operation the nosepiece 247 is inserted in the other of the nostrils of the subject, and the subject grips the mouthpiece 249 in his or her lips and exhales through the mouthpiece 249, as illustrated in FIG. 4(*e*).

In this second, subsequent exhalation cycle, the valve unit 251 is configured such as to direct the exhaled air flow through the other of the pair of blisters B, which acts to entrain the substance from the blister B.

In this mode of operation the same, or indeed different, substances can be delivered to each of the nasal cavities of the subject.

Following exhalation, the blister B is emptied.

In another mode of operation, where the blisters B contain different substances, and these substances are both to be delivered to one nasal cavity, the nosepiece 247 is not moved to the other nostril of the subject.

Following use of the delivery device, the interface assembly 211 is returned to the stowed, inoperative position, in this embodiment by pivoting the same relative to the housing 201, as illustrated in FIG. 4(*f*).

In moving the interface assembly 211 to the stowed position, the catch member 265 on the body member 235 of the interface assembly 211 is released from engagement with the recesses 289 in the rear surfaces of the opposing latch bodies 282 of the latch units 281.

This operation of the delivery device can then subsequently be repeated for the next pair of blisters B.

Finally, it will be understood that the present invention has been described in its preferred embodiments and can be modified in many different ways without departing from the scope of the invention as defined by the appended claims.

In one modification the delivery device could be modified to include a rotatable cartridge which includes a plurality of capsule-containing members 49, which are each successively indexed into the capsule-receiving chamber 23 of the capsule-receiving unit 16.

What is claimed is:

1. A nasal delivery device for delivering a substance to a nasal cavity of a subject, the delivery device comprising:

a removable nosepiece adapted unit including a nosepiece for fitting to the nasal cavity of the subject and a container-containing member which contains a substance-containing container containing substance to be delivered to the nasal cavity of the subject, wherein the container-containing member includes a flow passage in which the substance-containing container is disposed so as to be rotatable therewithin, and first and second apertures in a lateral wall thereof;

a container-receiving unit comprising a container chamber for receiving the container-containing member, wherein the container chamber includes an inlet and an outlet which is in fluid communication with the nosepiece, wherein the outlet of the container chamber receives the container-containing member and the container-containing member is a sealing fit in the container chamber;

a mouthpiece unit including a mouthpiece in fluid communication with the inlet of the container chamber and through which the subject in use exhales so as to deliver an exhalation flow through the mouthpiece and the flow passage of the container-containing member and entrain substance from the substance-containing container and deliver the same through the nosepiece; and a container-opening mechanism which is configured to open the substance-containing container when the substance-containing container is disposed in the container-containing member, wherein the container-opening mechanism comprises first and second piercing elements which are arranged to pass through the first and second apertures in the lateral wall of the container-containing member only when the container-containing member is sealingly fitted in the container chamber.

2. The delivery device of claim 1, wherein the inlet provides a flow restriction to an exhalation flow as delivered therethrough.

3. The delivery device of claim 2, wherein the inlet forms a seat on which a first end of the substance-containing container is seated prior to delivery of the exhalation flow through the flow passage.

4. The delivery device of claim 1, wherein the substance-containing container is a capsule containing a powdered substance.

* * * * *

UNITED STATES PATENT AND TRADEMARK OFFICE
CERTIFICATE OF CORRECTION

PATENT NO. : 10,398,859 B2
APPLICATION NO. : 14/798221
DATED : September 3, 2019
INVENTOR(S) : Per Gisle Djupesland et al.

It is certified that error appears in the above-identified patent and that said Letters Patent is hereby corrected as shown below:

In the Claims

Claim 1, Column 14, Lines 7-8:
"a removable nosepiece adapted unit including a nosepiece for fitting to the nasal cavity of the subject"
Should read:
--a removable nosepiece unit including a nosepiece adapted for fitting to the nasal cavity of the subject--.

Signed and Sealed this
Twelfth Day of November, 2019

Andrei Iancu
*Director of the United States Patent and Trademark Office*